US006383785B1

(12) United States Patent
Mueller et al.

(10) Patent No.: US 6,383,785 B1
(45) Date of Patent: *May 7, 2002

(54) SELF-ENHANCING, PHARMACOLOGICALLY CONTROLLABLE EXPRESSION SYSTEMS

(75) Inventors: Rolf Mueller; Hans-Harald Sedlacek, both of Marburg (DE)

(73) Assignee: Aventis Pharma Deutschland GmbH, Frankfurt (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/987,348

(22) Filed: Dec. 9, 1997

(30) Foreign Application Priority Data

Dec. 11, 1996 (DE) .......................... 196 51 443

(51) Int. Cl.[7] ............................... C12N 15/66

(52) U.S. Cl. ................. 435/91.41; 435/320.1; 435/325; 536/23.4; 536/24.1

(58) Field of Search ................ 435/69.1, 69.7, 435/325, 320.1, 440, 91.41; 536/23.4, 24.1

(56) References Cited

U.S. PATENT DOCUMENTS

| 5,589,362 A | * 12/1996 | Bujard et al. .............. 435/69.1 |
| 5,830,880 A | 11/1998 | Sedlacek et al. |
| 5,854,019 A | 12/1998 | Sedlacek et al. |
| 5,885,833 A | 3/1999 | Mueller et al. |
| 5,916,803 A | 6/1999 | Sedlacek et al. |

OTHER PUBLICATIONS

Ptashne, M. Nature. vol. 335, pp. 683–689, Oct. 1988.*
Pomerantz et al. Science. vol. 267, pp. 93–96, Jan. 1995.*
Das et al. Nature. vol. 374, pp. 657–660, Apr. 1995.*
Harrison, S. Nature. vol. 353, pp. 715–719, Oct. 1991.*
Morgan et al. Nucleic Acids Research. vol. 20(6), pp. 1293–1299, 1992.*
Fischer et al. The EMBO Journal. vol. 13(17), pp. 4105–4112, 1994.*
Dingwall et al. TIBS. vol. 16, pp. 478–481, Dec. 1991.*
Ho et al. Nature. vol. 382, pp. 822–826, Aug. 1996.*
Spencer et al. Science. vol. 262, pp. 1019–1024, Nov. 1993.*
Pruschy et al. Biology and Chemistry. vol. 1, pp. 163–172, Nov. 1994.*
Scmitz et al. The EMBO Journal. vol. 10 (12), pp. 3805–3817, 1991.*
Mountford et al. Trends in Genetics. vol. 11(5), pp. 179–184, 1995.*

Belshaw et al., "Controlling protein association and subcellular localization with a synthetic ligand that induces heterodimerization of proteins", *Proc. Natl. Acad. Sci. USA*, May 1996, pp. 4604–4607.

Ho et al., "Dimeric ligands define a role for transcriptional activation domains in reintiation", *Nature*, vol. 382, Aug. 29, 1996, pp. 822–826.

Chasman et al., "GAL4 Protein: Purification, Association with GAL80 Protein, and Conserved Domain Structure," *Molecular and Cellular Biology*, Jun. 1990, pp. 2916–2923.

Das et al., "Basal promoter elemetns as a selective determinant of transcriptional activator function," *Nature*, vol. 374, Apr. 13, 1995, pp. 657–660.

Tanaka et al., "The Oct–2 Glutamine–Rich and Proline–Rich Activation Domains Can Synergize with Each Other or Duplicates of Themselves To Activate Transcription," *Molecular and Cellular Biology*, Sep. 1994, pp. 6046–.

Papavassiliou et al., "Interaction of Cell and Virus Proteins with DNA Sequences Encompassing the Promoter/Regulatory and Leader Regions of the Herpes Simplex Virus Thymidine Kinase Gene," *J.Biol.Chem.*

Dingwall et al., Nuclear targeting sequences—a consensus?, *TIBS* 16, Dec. 1991, pp. 478–481. 530.

Kim et al., "Dimerization of a Specific DNA–Binding Protein on the DNA," *Science*, vol. 255, Jan. 10, 1992, pp. 203–206.

Brent et al., "A Eukaryotic Transcriptional Activator Bearing the DNA Specificity of a Prokaryotic Repressor," *Cell*, vol. 43, Dec. 1985, pp. 730–736.

Dingermann et al., "RNA polymerase III catalysed transcription can be regulated in *Saccharomyces cerevisiae* by the bacterial tetracycline repressor–operator system," *The EMBO Journal*, vol. 11, No. 4, 1992, 1487–1492.

(List continued on next page.)

*Primary Examiner*—James Ketter
(74) *Attorney, Agent, or Firm*—Heller Ehrman White and McAuliffe

(57) ABSTRACT

The invention relates to a nucleic acid construct which constitutes a self-enhancing expression system and which comprises the following components:

at least one first structural gene that encodes an active compound;

at least one second structural gene that encodes a transcription factor protein; and at least one activation sequence comprised of at least one sequence that binds the transcription factor protein and at least one promoter sequence;

wherein each activation sequence activates the expression of a structural gene and the expression of the transcription factor protein; and to the use of the nucleic acid construct for preparing a drug for treating diseases.

12 Claims, 16 Drawing Sheets

OTHER PUBLICATIONS

Dorai et al., Mammalian Cell Expression of Single–Chain Fv (sFv) Antibody Proteins and Their C–terminal Fusions with Interleukin–2 and Other Effector Domains, *Bio/Technology*, vol. 12, Sep. 1994, pp. 890–897.

Becker et al., FK–506–binding Protein: Three–dimensional Structure of the Complex with the Antagonist L–685,818, *J.Biol.Chem.*, vol. 268, No. 15, May 25, 1993, pp. 11335–11339.

Brown et al, "A mammalian protein targeted by G1–arresting rapamycin–receptor complex," *Nature*, vol. 369, Jun. 30, 1994, pp. 756–758.

Chiu et al., "RAPT1, a mammalian homolog of yeast Tor, interacts with the FKBPT12/rapamycin complex," *Proc. Natl. Acad. Sci. USA*, vol. 91, Dec. 1994, pp. 12574–12578.

Sabatini et al., "RAFT1: A Mammalian Protein That Binds to FKB12 in a Rapamycin–Dependent Fashion and Is Homologous to Yeast TORs," *Cell*, vol. 78, Jul. 15, 1994, pp. 35–43.

Spencer et al., "Controlling Signal Transduction with Synthetic Ligands," *Science*, vol. 262, Nov. 12, 1993, pp. 1019–1024.

Pruschy et al., "Mechanistic studies of a signalling pathway activated by the organic dimerizer FK1012," *Chemistry & Biology*, vol. 1, No. 3, 1994, pp. 163–172.

Clipstone et al., "Molecular Analysis of the Interaction of Calcineurin with Drug–Immunophilin Complexes," *J.Biol.Chem.*, vol. 269, No. 42, Oct. 21, 1994, pp. 26431–26437.

Goldsmith et al., "5' Nucleotide Sequences Influence Serum–Modulated Expression of a Human Dihydrofolat Reductase Minigene," *Molecular and Cellular Biology*, vol. 6, No. 3, Mar. 1986, pp. 878–886.

Sadasivan et al., "Genomic organization of the gene and a related pseudogene for a human folate binding protein," *Biochimica et Biophysica acta*, 1131 (1992) 91–94.

Stoner et al., "Mouse Cellular Retinoic Acid Binding Protein: Cloning, Complementary DNA Sequence, and Teratocarcinoma," *Cancer Research* 49, 1497–1504, Mar. 15, 1989.

Greaves et al., "Sequence, Function, and Regulation of the Vmw65 Genes of Herpes Simplex Virus Type 2 *Journal of Virology*, vol. 65, No. 12, Dec. 1991, pp. 6705–6713.

Schmitz et al., "The p65 subunit is responsible for the strong transcription activating potential of NF–Bk," *The EMBO Journal*, vol. 10, No. 12, 1991, pp. 3805–3817.

Van Kooten et al., "Cytokines and Intracellular Signals Involved in the Regulation of B–CLL Proliferation *Leukemia and Lymphoma*, vol. 12, 1993, pp. 27–33.

Craig A. Mullen, "Metabolic Suicide Genes in Gene Therapy," *Pharmac. Ther.*, vol. 63, 1994, pp. 199.

Harris et al., "Gene therapy for cancer using tumour–specific prodgru activation," *Gene Therapy* (1994), 1, 170–175.

Marasco et al., "Design, intracellular expression, and activity of a human anti–human immunodeficiency virus type 1 gp120 single–chain antibody," *Proc. Natl. Acad. Sci. USA*, vol. 90, Aug. 1993, pp. 7889–7893.

Schrewe et al., "Cloning of the Complete Gene for Carcinembryonic Antigen: Analysis of its Promoter Indicates a Region Conveying Cell Type–Specific Expression," *Molecular and Cellular Biology*, vol. 10, No. 6.

Brown et al., "Redundancy of Signal and Anchor Functions in the $NH_2$–Terminal Uncharged Region of Influenza Virus Neuramindase, a Class II Membrane Glycoprotein,"*Journal of Virology*, Oct. 1988, vol. 62, No. 10, pp.

Cunningham et al., "Neural Cell Adhesion Molecule: Structure, Immunoglobulin–Like DOmains, Cell Surface Modulation, and Alternative RNA Splicing," *Science*, vol. 236, May 15, 1987, pp. 799–805.

Lucibello et al., "Periodic cdc25C transcription is mediated by a novel cell cycle–regulated repressor element (CDE)," *The EMBO Journal*, vol. 14, No. 1, 1995, pp. 132–142.

Zwicker et al., "Cell cycle regulation of cdc25C transcription is mediated by the periodic repression of the glutamine–rich activators NF–Y and Sp1," *Nucleic Acids Research*, vol. 23, No. 19, 1995, pp. 3822–3830.

Zwicker et al., "Cell cycle regulation of the cyclin A, cdc25c and cdc2 genes is based on a common mechanism of transcriptional repression," *The EMBO Journal*, vol. 14, No. 18, 1995, pp. 4514–4522.

Morishita et al., "A Novel Promoter for Vascular Endothelial Growth Factor Receptor (flt–1) That Confers Endothelial–specific Gene Expression," *J.Biol.Chem.*, vol. 270, No. 46, Nov. 17, 1995, pp. 27948–27953.

Rosen et al., "The Location of Cis–Acting Regulatory Sequences in the Human T Cell Lymphotropic Virus Type III (HTLV–III/LAV) Long Terminal Repeat," *Cell*, vol. 41, Jul. 1985, pp. 813–823.

Blackwood et al., "Max: A Helix–Loop–Helix Zipper Protein That Forms a Sequence–Specific DNA–Binding Complex with Myc," *Science*, vol. 251, Mar. 8, 1991, pp. 1211–1217.

Truss et al., "Steroid Hormone Receptors: Interaction with Deoxyribonucleic Acid and Transcription Factors," *Endocrine Reviews*, vol. 14, No. 4, Aug. 1993, pp. 459–479.

Malim et al., "The HIV–1 rev trans–activator acts through a structured target sequence to activate nuclear export of unspliced viral mRNA," *Nature*, vol. 338, Mar. 16, 1989, pp. 254–257.

Kjems et al., "Structural analysis of the interaction between the human immunodeficiency virus Rev protein and the Rev response element," *Proc. Natl. Acad. USA*, vol. 88, Feb. 1991, pp. 683–687.

Huang et al., "A Novel Hepatitis B Virus (HBV) Genetic Element with Rev Response Element–Like Properties That is Essential for Expression of HBV Gene Products," *Molecular and Cellular Biology*, vol. 13, Dec. 1993.

Daly et al., "Specific binding of HIV–1 recombinant Rev protein to the Rev–responsive element in vitro, *Nature*, vol. 342, Dec. 14, 1989, pp. 816–819.

Emerman et al., "The rev Gene Product of the Human Immunodeficiency Virus Affects Envelope–Specific RNA Localization," *Cell*, vol. 57, Jun. 30, 1989, pp. 1155–1165.

Felber et al., "rev protein of human immunodeficiency virus type 1 affects the stability and transport of the viral mRNA," *Proc. Natl. Acad. Sci. USA*, vol. 86, Mar. 1989, pp. 1495–1499.

Fischer et al., "Evidence that HIV–1 Rev directly promotes the nuclear export of unsplied RNA," *The EMBO Journal*, vol. 13, No. 17, 1994, pp. 4105–4112.

Zapp et al., "Sequence–specific RNA binding by the HIV–1 Rev protein," *Nature*, vol. 342, Dec. 7, 1989, pp. 714–716.

Malim et al., "HIV–1 Structural Gene Expression Requires the Binding of Multiple Rev Monomers to the Viral RRE: Implications for HIV–1 Latency," *Cell*, vol. 65, Apr. 19, 1991, pp. 241–248.

Iwai et al., "Recognition of the high affinity binding site in rev–response element RNA by the Human Immunodeficiency Virus type–1 rev protein," *Nucleic Acids Research*, vol. 20, No. 24, 1992, pp. 6465–6475.

Bogerd et al., "Identification of a Novel Cellular Cofactor for the Rev/Rex Class of Retroviral Regulatory Proteins," *Cell*, vol. 82, Aug. 11, 1995, pp. 485–494.

Tiley et al., "Conserved Functional Organization of the Human Immunodeficiency Virus Type 1 and Visna Virus Rev Proteins," *Journal of Virology*, vol. 65, No. 7, Jul. 1991, pp. 3877–3881.

Cullen, "Mechanism of Action of Regulatory Proteins Encoded by Complex Retroviruses," *Microbiological Reviews*, Vo. 65, No. 3, Sep. 1992, pp. 375–394.

Guddat et al., "Protein–Mediated Nuclear Export of RNA: 5S rRNA Containing Small RNPs in *Xenopus Oocytes*," *Cell*, vol. 60, Feb. 23, 1990, pp. 619–628.

Fantozzi et al., "Thermostable Inhibitor of cAMP–dependent Protein Kinase Enhances the Rate of Export of the Kinase Catalytic Subunit from the Nucleus," *J.Biol.Chem.*, vol. 269, No. 4, Jan. 28, 1994, pp. 2676–2686.

Wen et al., "Heat–stable Inhibitors of cAMP–dependent Protein Kinase Carry a Nuclear Export Signal," *J.Biol.Chem.*, vol. 269, No. 31, Dec. 23, 1994, pp. 32214–32220.

Cochrane et al., "Identification of Sequences Important in the Nuclear Localization of Human Immunodeficiency Virus Rev: Relevance of Nucleolar Localization to Function," *Journal of Virology*, vol. 64.

Kjems et al., "Specific binding of a basic peptide from HIV–1 Rev," *The EMBO Journal*, vol. 11, No. 3, 1990, pp. 1119–1129.

Wen et al., "Identification of a Signal for Rapid Export of Proteins from the Nucleus," *Cell*, vol. 82, Aug. 11, 1995, pp. 463–473.

Fischer et al., The HIV–1 Rev Activation Domain Is a Nuclear Export Signal That Accesses an Export Pathway Used by Specific Cellular RNAs," *Cell*, vol. 82, Aug. 11, 1995, pp. 475–483.

Mountford et al., "Internal ribosome entry sites and dicstronic RNAs in mammalian transgenesis," *TIG*, vol. 11, No. 5, pp. 179–184.

Kaufman et al., "Improved vectors for stable expression of foreign genes in mammalian cells by use of the untranslated leader sequence from EMC virus," *Nucleic Acids Research*, vol. 19, No. 16, 1991, pp. 4485–.

Morgan et. al, "Retroviral vectors containing putative internal ribosome entry sites: development of a polycistronic gene transfer sys and applications to human gene therapy," *Nucleic Acids Research*, vol. 20.

Dirks et al., "Picstronic transcription units for gene expression in mamallian cells," vol. 128, 1993, pp. 247–249.

Sugimoto et al., "Efficient Expression of Drug–selectable Genes in Retroviral Vectors Under Control of an Internal Ribosome Entry Site," *Bio/Technology*, vol. 12, Jul. 1994, pp. 694–698.

Stickney et al., "Biologic response modifiers: therapeutic approaches to lymphoproliferative diseases," *Current Opinion in Oncology 1992* 4:847–855.

Imai et al., "C33 Antigen and M38 Antigen Recognized by Monoclonal Antibodies Inhibitory to Synctium Formation by Human T Cell Leukemia Virus Type 1 are Both Members of the Transmembrane 4 Superfamily and Associated with Each Other and with CD4 or CD8 in T Cells," *The Journal of Immunology*, vol. 151.

* cited by examiner

FIG. 16

| COMPONENT b) | COMPONENT c) | COMPONENT d) | COMPONENT f) | | COMPONENT g) | COMPONENT h) | | |
|---|---|---|---|---|---|---|---|---|
| SEQUENCE FOR BINDING THE Gal4 PROTEIN + AV10 BASAL PROMOTER | IMMUNO-GLOBULIN SIGNAL SEQUENCE + β-GLUCU-RONIDASE | SEQUENCE FOR BINDING THE Gal4 PROTEIN + cdc25C PROMOTER ELEMENT | HOV-1 VE16 ACTIVATION DOMAIN | RAC-ANTI-CYCLOE-PORIN & FV (PROTEIN A) | SEQUENCE FOR BINDING THE Gal4 PROTEIN + cdc25C PROMOTER ELEMENT | RAC-ANTI-CYCLOE-PORIN & FV (PROTEIN B) | DNA-BINDING DOMAIN OF THE Gal4 PROTEIN | gv40 NLS | HSV1 VP16 TRANSACTIVATION DOMAIN |

5'  ...  3'

SELF-ENHANCING, PHARMACOLOGICALLY CONTROLLABLE EXPRESSION SYSTEMS

BACKGROUND OF THE INVENTION

The invention relates to a self-enhancing nucleic acid construct that comprises at least one regulatory sequence coupled to at least one structural gene and at least one transcription factor protein gene.

Despite various approaches taken in gene therapy, preclinical and clinical investigation results so far obtained indicate that two fundamental problems remain unsolved. One is insufficient transgenic expression from target cells in vitro or in vivo due to intracellular shutdown processes. The second is inadequate control of transgenic expression.

In an attempt to rectify these shortcomings of the prior art, Rivera et al. (Nature Med. 2, 1028 (1996)), Belshaw et al. (PNAS USA 93, 4604 (1996)) and Ho et al. (Nature 382, 822 (1996)) have developed the first techniques for external control of transgenic expression. These approaches are based on adding the active compound rapamycin, which couples two subunits together. The resulting coupling product acts as a transcription factor. The first subunit constitutes a fusion protein formed between a DNA-binding protein and FK506-binding protein (FKBP), which protein also binds rapamycin. The second subunit is a fusion protein which is formed between a protein FRAP, which also binds to rapamycin, and the activation sequence of transcription factor protein NF-KB.

The functional transcription factor protein that is produced by the coupling of these two subunits with rapamycin in turn activates the sequence in the transgene for activating the structural gene.

The advantage of this external approach is that the expression of a structural gene can be switched on or switched off by adding or removing, respectively, the active compound rapamycin. However, this approach does not solve the problem of inadequate expression of a structural gene. Accordingly, the need remains for an approach to increase transgenic expression.

SUMMARY OF THE INVENTION

The invention fulfills the unmet needs of the art by providing nucleic acid constructs, compositions containing the constructs and methods of their use to achieve high transgenic expression. The invention does this by incorporating a positive feedback system within the nucleic acid construct itself. The resulting system is termed herein a "self-enhancing expression system."

In one embodiment of the invention a nucleic acid construct is provided that comprises:
- at least one first structural gene that encodes an active compound;
- at least one second structural gene that encodes a transcription factor protein; and
- at least one activation sequence comprised of at least one sequence that binds the transcription factor protein and at least one promoter sequence;

wherein each activation sequence activates the expression of a structural gene and the expression of the transcription factor protein.

In another embodiment of the invention a nucleic acid construct is provided that comprises:
- at least one first structural gene that encodes an active compound;
- at least one second structural gene that encodes a transcription factor protein; and
- at least one activation sequence comprised of at least one sequence that binds said transcription factor protein and at least one pharmacological control module that comprises, in serial order, at least one promoter, at least one fusion protein gene coding for an activation domain of a transcription factor protein and coding for a coupling substance protein, at least one promoter, at least one fusion protein gene coding for a DNA-binding protein and coding for a second coupling substance protein, and at least one activation sequence that comprises a site for the DNA-binding protein wherein each activation sequence activates the expression of a structural gene and the expression of the transcription factor protein.

In still another embodiment of the invention a nucleic acid construct provided that comprises:
- at least one first structural gene that encodes an active compound;
- at least one second structured gene that encodes at least one first fusion protein that comprises an activation domain of a transcription factor protein, and a sequence that binds a coupling substance;
- at least one third structural gene that encodes at least one second fusion protein that comprises a protein that binds a coupling substance and a DNA-binding protein;
- at least one activation sequence comprised of at least one sequence that binds said second fusion protein coupled to said first fusion protein by a coupling substance and at least one promotor sequence;

wherein each activation sequence activates the expression of at least one of aid structural genes.

Further embodiments readily will be apparent to the skilled artisan, pon reading the specification and appended claims.

The Self-enhancing Expression System

In its simplest embodiment, the novel self-enhancing expression system comprises the following components:
a) at least one sequence a) and/or a') for binding a transcription factor protein d),
b) at least one promoter sequence b) and/or b'),
c) at least one structural gene c) encoding an active compound, and
d) at least one gene encoding a transcription factor protein d) which binds to component a).

In conformity with the invention, components a) and/or a') and b) and/or b') constitute a sequence for activating transcription of structural gene c) and for activating expression of transcription factor protein d).

In a preferred form according to the invention, the components can be arranged as depicted in FIG. 1.

The binding sequences a) and a') can be identical or different and bind the transcription factor d).

The promoter sequences [components b) and b')] can be identical or different. Low-level activation of the promoter sequences b) and b') results in low-level expression of the structural gene [component c)] and of the gene for the transcription factor protein d) [component d)]. Transcription factor protein d) made thereby, in turn binds to binding sequences [components a) and a')]. This binding in turn activates promoter sequences b) and b'), bringing about an enhanced expression of both the structural gene and the gene for the transcription factor protein d). This enhanced expression itself results in a higher amount of transcription factor protein d), which feeds-back and further stimulates this system.

According to the invention, the arrangement of the components as depicted in FIG. 1 can be supplemented (i.e. "appended" at the upstream end) with genes encoding a nuclear export signal (NES) and a nuclear export factor (NEF) at the 3' end of the structural gene. Expression of the NEF is under the control of an additional promoter (component b'''). This additional promoter sequence may be identical to or different from any part of the activation sequences [components a) and b) and/or a') and b')] shown in FIG. 2.

The nuclear export signal (NES) is a nucleotide sequence that impedes the transport of a pre-messenger RNA, which is linked to it, through the nuclear membrane. The NES consequently constitutes, on its own, a nuclear retention signal (NRS). However, if the NRS binds an export protein, here termed "nuclear export factor" or "NEF", the NRS gains the function of an NES. This is because the nuclear export factor (NEF) mediates the transport of the NES-containing premessenger or messenger RNA out of the cell nucleus and into the cytoplasm. An NES-containing premessenger or messenger RNA consequently is secreted out of the cell nucleus by its being bound to the NEF as described by Fischer et al., Cell 82, 475 (1995).

In accordance with the invention, components c) and d) also can be linked to each other (i.e. "mutually linked") by an internal ribosome entry site (IRES) instead of through linkage with components a') and b'). Such IRESs lead to the expression of two DNA sequences which are linked to each other by way of the IRES.

The linkage by way of an IRES can be effected, for example, as depicted in FIG. 3.

This arrangement also ensures to the same extent that when promoter sequence b) has been subjected to low-level activation, the gene for the transcription factor protein [component d)] is also expressed, by way of the IRES sequence. This expression occurs while the structural gene [component c)] is expressed. In addition, the transcription factor protein binds to binding sequence a), which enhances activation of promoter sequence b), enhances expression of structural gene c) and, once again via the IRES sequence, also enhances expression of the transcription factor protein d) gene.

The arrangement, according to the invention, of individual components as depicted in FIGS. 1–3 is a self-enhancing expression system that operates as shown in FIG. 4. The self-enhancing expression system can be extended by stringing together several identical or different sequences for structural genes [components c), c') and c'')]. These structural genes are interlinked by identical or different IRES sequences, or through binding sequence a), promoter sequence b') and promoter sequence b''). A representative arrangement is depicted in FIG. 5. The self-enhancing expression system also can be extended by stringing together several identical or different genes for transcription factor protein d) [components d), d') and d'')]. One representative example is shown by FIG. 6, which indicates linking by IRES sequences. The IRES sequences optionally, may be the same sequence.

Binding sequence a) preferably is one type in all activation sequences. All transcription factor proteins d), d') and d'') should bind to this binding sequence. When the binding sequences are not the same type (e.g. when component a is not the same as component a'), then the transcription factor proteins [components d), d') and d'')] should bind to all of the binding sequences. The activation sequences are preferably designed or selected such that they are recognized by all products of transcription factor proteins d), d') and d'').

In a similar manner as shown in FIG. 2, the components of FIG. 3 can be supplemented with genes encoding a nuclear export signal (NES) and a nuclear export factor. This arrangement with an NES gene at the 3' end of the structural gene [component c)] and an NEF gene is shown in FIG. 7. In this last example, NEF is activated separately via an additional promoter sequence component b'''). The component b''' sequence can be identical or non-identical to components a) and b).

The Pharmacologically Controllable Promoter Module

In its simplest form, the novel pharmacologically controllable promoter module ("pharmacological control module") comprises the following components:

e) at least one promoter sequence,
f) at least one gene encoding a fusion protein f) which comprises an activation domain of a transcription factor protein and a coupling substance [component j)]-binding protein A,
g) at least one further promoter sequence [identical or non-identical to component e)] or at least one IRES,
h) at least one gene encoding a fusion protein h) which comprises a DNA-binding domain and a coupling substance [component j)]-binding protein B,
i) at least one activation sequence having a site for binding fusion protein h), and
j) at least one coupling substance j) which comprises both a site A) for binding protein A in the fusion protein f) [expression product of component f)] and a site B) for binding protein B) in fusion protein h) [expression product of component h)].

Components e–i) can be arranged serially, as for example, in accordance with the scheme shown in FIG. 8. This arrangement ensures that fusion proteins f) and h) [components f) and h)] are expressed when promoter sequences e) and g) are activated. When the coupling substance [component j)] is present, the two fusion proteins are linked to each other ("mutually linked") to form a functional transcription factor protein for activating the activation sequence [component i)]. In this embodiment of the invention, the promoter module, which is comprised of individual components, functions in the presence of a coupling substance such as component j). The module becomes functional upon addition of the coupling substance component j). FIG. 9 shows an example of this embodiment.

The self-enhancing, Pharmacologically Controllable Expression System

The self-enhancing expression system may be combined with a pharmacologically controllable promoter module. This combination is then effected, for example, by inserting a pharmacologically controllable promoter module [components e) to i)] into the self-enhancing expression system (see FIGS. 1, 2, 3 or 7) in place of the promoter sequence (component b) and/or b')). The construction of this combined nucleotide sequence is illustrated, by way of example, in FIG. 10. In this example, a structural gene is transcribed only when fusion proteins f) and h) [expression products of components f) and h)] are linked by coupling substance component j) to form a transcription factor protein.

Alternatively, or in addition, the pharmacologically controllable promoter module can be inserted into the self-enhancing expression system in place of the gene for the transcription factor protein [component d)], the sequence for binding transcription factor protein d) [component a)] and the promoter sequence b) [component b)]. In this case, the binding component h) site should be attached, at least by its 5' end, to one of the promoter sequences e) and g). The construction of this combined nucleotide sequence is exemplified in FIG. 11.

The self-enhancing system can be combined with the pharmacologically controllable promoter module in other ways as well. For example, FIG. 8 shows that promoter sequence (component b''')) of the NEF (see FIG. 2 or 7) can be replaced by a pharmacologically controllable promoter module. One way of constructing this nucleotide sequence is shown in FIG. 12.

The nucleic acid constructs of the invention advantageously consist of DNA. The term "nucleic acid construct" denotes an artificial structure comprising nucleic acid and which can be transcribed in a target cell. A nucleic acid construct advantageously is inserted into a vector. In this context, a plasmid vector or viral vector is particularly desirable.

Depending on the choice of promoter sequence, a novel nucleic acid construct can be used to express a structural gene [component c)] non-specifically. Alternatively, the expression is further controlled by cell specificity, virus specificity, a defined condition, or a cell cycle condition. The structural gene preferably encodes a pharmacologically active compound or enzyme which cleaves an inactive precursor of a drug to form an active drug. The structural gene further can be designed to express an enzyme—ligand fusion protein. In this case, the ligand may bind to a cell surface. Most preferred in this context is a ligand that binds to the surface of a proliferating endothelial cell or tumour cell.

The present invention also relates to cells, particularly yeast or mammalian cells, which harbour a novel nucleic acid construct. In a particularly desirable embodiment, a nucleic acid construct is introduced into a cell line that is transfected by the addition or administration of a coupling substance [component j)]. Addition of the coupling substance stimulates expression of the structural gene. Cells that contain these constructions can be used to prepare a pharmaceutical composition. However, the cells also can be administered to a patient as a therapeutic agent, or pharmaceutical composition, to treat a disease. Alternatively, the novel nucleic acid construct can be incorporated into a vector and directly administered locally or parenterally into a patient. In use, the construct is designed for a particular disease such that the construct expresses one or more proteins, or nucleic acid that prevents or ameliorates one or more symptoms of the disease. The amount of nucleic acid construct that is to be used in this context is determined by route of administration, the status of the patient, and by the nature of the disease, as is known to a skilled artisan.

In the case of administration directly to a patient, a coupling substance [component j)] additionally may be administered in order to express the structural gene. The coupling substance causes formation of a complete transcription factor protein by coupling fusion protein f) with fusion protein h) within transfected cells, as shown in FIG. 9. Consequently, the transfected cells only express the structural gene as long as the coupling substance is present in the body. The duration and strength of the expression can be controlled by administering the coupling substance.

A preferred use of the novel nucleic acid construct consequently consists in the treatment of a disease, with the provision of the drug comprising introducing a nucleic acid construct into a target cell and expressing the construct in a non-specific, virus-specific or target cell-specific and/or cell cycle-specific manner by means of administering a coupling substance.

Nucleic acid constructs of the invention can be used to prepare a pharmaceutical composition by way of synthesis in a cell. In this context, a cell is transformed with a DNA construct of the invention. The transformed cell then is cultured to obtain a clone of cells, thereby creating multiple copies of the DNA construct. Preferably, gene amplification is used to increase the number of copies of the DNA construct in each cell. After culturing the transformed cell to obtain multiple copies of the DNA construct, the DNA construct can be purified from the cultured cells. E. coli is preferred as the cultured cell to obtain multiple copies of the DNA construct. The purified DNA is used as a component in a pharmaceutical composition by mixing with other substance(s) such as buffer, salts, or other excipients as are known in the art.

The novel nucleic acid constructs do not occur in this form in nature, i.e. the structural gene for the active compound or for an enzyme or for a ligand/enzyme fusion protein is not naturally combined with the novel nucleic acid sequences to form a self-enhancing expression system. This system is also not naturally combined with a pharmacologically controllable promoter module.

Preferred structural genes, which are incorporated into a self-enhancing pharmacologically controllable expression system, encode pharmacologically active compounds. These active compounds are proteins and glycoproteins which are selected from the group consisting of cytokines, growth factors, receptor cytokines or growth factors, antibodies or antibody fragments, proteins having an antiproliferative or cytostatic effect, angiogenesis inhibitors, thrombosis-inducing proteins, coagulation inhibitors, blood plasma proteins, complement-activating proteins, viral and bacterial coat substances, hormones, peptides having an effect on the circulation, neuropeptides, enzymes and mediators and fusion proteins which comprise at least two of these proteins or glycoproteins.

Detailed Description of the Components of the Self-enhancing, Pharmacologically Controllable Expression System 1) Activation Sequences and Transcription Factor Proteins for Self-enhancing Expression Systems Within the meaning of the invention, the transcription factor protein d) [gene product of component d)] binds specifically to the relevant binding sequence a) [component a)] which, for its part, activates the 3'-adjacent promoter sequence b) (or b' or b").

Components a) and b) consequently constitute an activation sequence which comprises a sequence for binding the relevant transcription factor protein d).

On the other hand, the transcription factor protein d) must comprise a binding domain which is specific for the corresponding binding sequence of the activator sequence [component a)], as well as a transactivation domain. An additional nuclear localization signal (NLS) promotes the interaction with the activation sequence a).

Examples of nucleic acid constructs which meet this prerequisite are:

Embodiment A), Comprising 1. an activation sequence comprising a component a)
   having at least one sequence (SEQ ID NO:1) [e.g. nucleotide sequence: 5'-CGGACAACTGTT-GACCG-3'] for binding the Gal4 protein (Chasman and Kornberg, Mol. Cell Biol. 10, 2916 (1990)) and, at its 3' end, a component b), which comprises:
   the basal SV40 promoter
      (nucleic acids 48 to 5191; Tooze (ed.), DNA Tumor Viruses (Cold Spring Harbor N.Y., (1980), New York; Cold Spring Harbor Laboratory),
   the c-fos promoter (Das et al., Nature 374, 657 (1995)) and, at its 3' end, the HSV1 VP16 acid transactivation domain (TAD) (amino acids 406 to 488; Treizenberg et al., Genes Developm. 2, 718 (1988); Triezenberg, Curr. Opin. Gen. Developm. 5, 190 (1995)), the U2 sn RNA promoter and (at its 3' end) the HSV1 VP16 TAD or at least a sequence of the activation domain of Oct-2 (amino acids 438 to 479; Tanaka et al., Mol. Cell Biol. 14, 6046 (1994); Das et al., Nature 374, 657 (1995)) or the HSV TK promoter (Papavassiliou et al., J. Biol. Chem. 265, 9402 (1990); Park et al., Molec. Endocrinol. 7, 319 (1993)) or another non-specific, cell-specific, virus-specific or cell cycle-specific or metabolically activatable promoter, and 2. the gene for the relevant transcription factor protein d) [component d)] containing the cDNA for the DNA-binding domain of the Gal4 protein (amino acids 1 to 147; Chasman and Kornberg, Mol. Cell Biol. 10, 2916 (1990)), to the 3' end of which is attached the SV40 nuclear localization signal (NLS) (SV40 large T; amino acids 126 to 132: e.g. (SEQ ID NO:2) PKKKRKV; Dingwall et al., TIBS 16, 478 (1991)), to the 3' end of which is attached the HSV-1 VP16 acid transactivation domain (TAD) (amino acids 406 to 488; Triezenberg et al., Genes Developm. 2, 718 (1988); Triezenberg, Curr. Opin. Gen. Developm. 5, 190 (1995)).

Embodiment B) Comprising 1. an activation sequence comprising a component a)

containing at least one sequence (SEQ ID NO:3) [e.g. nucleotide sequence 5'-TACTGTATGTACA-TACAGTA-3'] for binding the LexA protein [LexA operator; Brent et al., Nature 612, 312 (1984)] and, at its 3' end, a component b) which comprises:

the SV40 basal promoter (nucleic acids 48 to 5191; Tooze (ed.), DNA Tumor Viruses (Cold Spring Harbor N.Y., (1980) New York; Cold Spring Harbor Laboratory) or another promoter (see Embodiment A), and 2. the gene for the affiliated transcription factor protein d) [component d)] containing the cDNA for the DNA-binding domain of the LexA protein (amino acids 1 to 81; Kim et al., Science 255, 203 (1992)) or the whole LexA protein (amino acids 1 to 202; Brent et al., Cell 43, 729 (1985)) to the 3' end of which is attached the SV40 nuclear localization signal (NLS) (SV40 large T; amino acids 126 to 132: e.g. (SEQ ID NO:2) PKKKRKV; Dingwall et al., TIBS 16, 478 (1991)), to the 3' end of which are attached the HSV-1 VP16 acid transactivation domains (TAD) (amino acids 406 to 488; Triezenberg et al., Genes Developm. 2, 718 (1988); Triezenberg, Curr. Opin. Gen. Developm. 5, 190 (1995)).

Embodiment C) Comprising 1. an activation sequence comprising a component a)

containing at least one lac operator sequence (SEQ ID NO:4) (e.g. nucleotide sequence: 5'-GAATTGTGAGCGCTCACAATTC-3') for binding the lac I repressor protein (Fuerst et al., PNAS USA 86, 2549 (1989); Simons et al., PNAS USA 81, 1624 (1984)) and, at its 3' end, a component b) which comprises:

the SV40 basal promoter (nucleic acids 48 to 5191; Tooze (ed.) DNA Tumor Viruses (Cold Spring Harbor New York, N.Y., P(1980) Cold Spring Harbor Laboratory) or another promoter (see Embodiment A), and 2. the gene for the affiliated transcription factor protein d) [component d)] containing the cDNA for the lac repressor (lac I) protein (Brown et al., Cell 49, 603 (1987); Fuerst et al., PNAS USA 86, 2549 (1989)), to the 3' end of which is attached the SV40 nuclear localization signal (NLS) (SV40 large T; amino acids: 126–132; e.g. (SEQ ID NO:2) PKKKRKV; Dingwall et al., TIBS 16, 478 (1991)), to the 3' end of which is attached the HSV-1 VP16 acid transactivation domain (TAD) (amino acids: 406–488; Triezenberg et al., Genes Developm. 2, 718 (1988); Triezenberg, Curr. Opin. Gen. Developm. 5, 190 (1995)).

Embodiment D) Comprising 1. an activation sequence comprising a component a)

containing at least one tetracycline operator (tet O) sequence (SEQ ID NO:5) (e.g. nucleotide sequence: 5'-TCGAGTTTACCACTCCCTATCAGTGATAGAG AAAAGTGAA AG-3') for binding the tetracycline repressor (tet R) protein and, at its 3' end, a component b) which comprises:

the SV40 basal promoter (nucleic acids 48 to 5191; Tooze (ed.) DNA Tumor Viruses (Cold Spring Harbor New York, (1980) N.Y., Cold Spring Harbor Laboratory) or another promoter (see Embodiment A) and 2. the gene for the affiliated transcription factor protein d) [component d)] containing the cDNA for the tetracycline repressor (tet R) protein (Gossen et al., PNAS USA 89, 5547 (1992); Dingermann et al., EMBO J. 11, 1487 (1992)) and, at its 3' end, the SV40 nuclear localization signal (NLS) (SV40 large T; amino acids 126–132; e.g. (SEQ ID NO:2) PKKKRKV; Dingwall et al., TIBS 16, 478 (1991)) and, at its 3' end, the HSV-1 VP16 acid transactivation domain (TAD) (amino acids: 406–488; Triezenberg et al., Genes Developm. 2, 718 (1988); Triezenberg, Curr. Opin. Gen. Developm. 5, 190 (1995)).

Embodiment E) Comprising 1. an activation sequence comprising a component a)

containing at least one sequence (SEQ ID NO:6) [e.g. nucleotide sequence 5'-TAATGATGGGCG-3'] for binding the ZFHD-1 protein (Pomerantz et al., Science 267, 93 (1995)) and, at its 3' end, a component b) which comprises:

the basal SV40 promoter (nucleic acids 48 to 5191; Tooze (ed.), DNA Tumor Viruses (Cold Spring Harbor N.Y., (1980) New York, Cold Spring Harbor Laboratory) or another promoter (see Embodiment A) and 2. the gene for the affiliated transcription factor protein d) [component d)] containing the cDNA for the ZFHD1-protein (Pomerantz et al., Science 267, 93 (1995)) and, at its 3' end, the SV40 nuclear localization signal (NLS) (SV40 large T; amino acids 126 to 132: e.g. (SEQ ID NO:2) PKKKRKV; Dingwall et al., TIBS 16, 478 (1991)) and, at its 3' end, the HSV-1 VP16 acid transactivation domain (TAD) (amino acids 406 to 488; Triezenberg et al., Genes Developm. 2, 718 (1988); Triezenberg, Curr. Opin. Gen. Developm. 5, 190 (1995).

2) Pharmacologically Controllable Promoter Modules

In accordance with the invention, the following genes are specific components of the pharmacologically controllable promoter modules (see FIGS. 8 and 9 as well):

for the fusion protein f) [component f)]:
  the gene for the activation domain of a transcription factor protein, and
  at least one gene for a protein A which binds the coupling substance j), where appropriate
  supplemented with a nuclear localization signal (NLS)

for the fusion protein h) [component h)]:
  at least one gene for a protein B which binds the coupling substance j) and
  the gene for a protein which binds to the DNA of the activation sequence [component i)]

for the coupling substance
  the component j) having at least one site for binding the protein A and for binding the protein B and the activation sequence comprising a site for binding the fusion protein h) [component h)] and a promoter element for the component i).

The choice of the coupling substance [component j)] inevitably determines the nature of the component j)-binding proteins A and B in components f) and h), respectively. In this context, the component j)-binding proteins A and B in components f) and h) can be identical or non-identical. Identical component j)-binding proteins A and B can be used, in particular, when the coupling substance [component j)] possesses several identical binding sites. Within the meaning of the invention, however, nonidentical, component j)-binding proteins A and B are preferred in components f) and h).

This means that the coupling substance [component j)] is bound by fusion protein f) [component f)] at a site which is different from that at which it is bound by fusion protein h) [component h)], so that fusion proteins f) and h) do not compete with each other for binding to the coupling substance.

Coupling substances can be used which are already known to bind to particular cellular proteins whose genes can be used in components f) and h) of the pharmacologically controllable promoter.

However, this invention also relates, in particular, to using monoclonal antibodies, and recombinant antibodies derived therefrom, or their fragments, which bind to the coupling substance j). The insertion of these monoclonal antibodies, in particular their recombinant Fv fragments, into fusion proteins f) and h) [components f) and h)] constitutes a particular feature of this invention. In this context, recombinant Fv fragments which recognize different binding sites (epitopes of the A and B-binding sites, respectively) on the coupling substance [component j)] are preferably employed in the fusion proteins [components f) and h)].

Within the meaning of the invention, use can be made of both murine and human monoclonal antibodies. The murine monoclonal antibodies are preferably employed in humanized form. The humanization is effected in the manner described by Winter et al. (Nature 349, 293 (1991)) and Hoogenbooms et al. (Rev. Tr. Transfus. Hemobiol. 36, 19 (1993)). Antibody fragments are prepared in accordance with the state of the art, for example in the manner described by Winter et al., Nature 349, 293 (1993); Hoogenboom et al., Rev. Tr. Transfus. Hemobiol. 36, 19 (1993); Girol, Mol. Immunol. 28, 1379 (1991) and Huston et al., Int. Rev. Immunol. 10, 195 (1993).

Recombinant antibody fragments are prepared directly from existing hybridomas or are isolated from libraries of murine or human antibody fragments (Winter et al., Annu. Rev. Immunol. 12, 433 (1994)) using phage-display technology (Smith, Science 228, 1315 (1985)). These antibody fragments are then employed directly, at the genetic level, for fusing with other proteins or peptides [with the activation domain of a transcription factor protein (component f) or with the DNA-binding protein (component h)].

In order to prepare recombinant antibody fragments from hybridomas, the genetic information which encodes the antigen-binding domains (VH and VL) of the antibodies is obtained by isolating the mRNA, reverse transcribing the RNA into cDNA and then amplifying the cDNA by means of the polymerase chain reaction (Saiki et al., Science 230, 1350 (1985)) using oligonucleotides which are complementary to the 5' and 3' ends, respectively, of the variable fragments (Orlandi et al., PNAS-USA 86,3833 1989). The VH and VL fragments are then cloned into bacterial expression vectors, for example in the form of Fv fragments (Skerra & Plückthun, Science 240, 1038 (1988), single-chain Fv fragments (scFv) (Bird et al., Science 242, 423 (1988); Huston et al., PNAS-USA 85 5879 (1988)) or Fab fragments (Better et al., Science 240, 1041 (1988)).

New antibody fragments can also be isolated directly from antibody libraries (immune libraries or naive libraries) of murine or human origin using phage-display technology. In the phage display of antibody fragments, the antigen-binding domains are cloned, either into the phage genome (McCafferty et al., Nature 348, 552 (1990)) or into phagemid vectors (Breitling et al., Gene 104, 147 (1991)), in the form of scFv fragments (McCafferty et al., Nature 348, 552 (1990)) or Fab fragments (Hoogenboom et al., Nucl. Acid Res. 19, 4133 (1991); Barbas et al., PNAS USA 88, 7978 (1991)) as fusion proteins together with the g3P coat protein of filamentous bacteriophages. Antigen-binding phages are selected on antigen-loaded plastic receptacles (panning) (Marks et al., J. Mol. Biol. 222, 581 (1991)), on antigen-conjugated, paramagnetic beads (Hawkins et al., J. Mol. Biol. 226, 889 (1992)) or by binding to cell surfaces (Marks et al., Bio/Technol. 11, 1145 (1993)).

Immune libraries are prepared by PCR amplification of the variable antibody fragments from the B lymphocytes of immunized animals (Sastry et al., PNAS-USA 86, 5728 (1989); Ward et al., Nature 341, 544 (1989); Clackson et al., Nature 352, 624 (1991)) or of patients (Mullinax et al., PNAS-USA 87, 8095 (1990); Barbas et al., PNAS-USA 88, 7978 (1991)). For this, use is made of combinations of oligonucleotides which are specific for murine (Orlandi et al., PNAS-USA 86, 3833 (1989); Sastry et al., PNAS-USA 86, 5728 (1989)) or human immunoglobulin genes (Larrick et al., BBRC 160, 1250 (1989)), or are specific for the human immunoglobulin gene families (Marks et al., Eur. J. Immunol. 21, 985 (1991)).

Native libraries can be prepared by using non-immunized donors as the source of the immunoglobulin genes (Marks et al., J. Mol. Biol. 222, 581 (1991)). Alternatively, immunoglobulin germ line genes can be used to prepare semisynthetic antibody repertoires, with the complementarity-determining region 3 of the variable fragments being amplified by means of PCR using degenerate primers (Hoogenboom & Winter, J. Mol. Biol. 227, 381 (1992); Barbas et al., PNAS-USA 89, 4457 (1992); Nissim et al., EMBO J. 13, 692 (1994); Griffiths et al., EMBO J. 13, 3245 (1994)). As compared with immune libraries, the so-called single-pot libraries have the advantage that antibody fragments against a large number of antigens can be isolated from one single library (Nissim et al., EMBO J. 13, 692 (1994)).

The affinity of antibody fragments can be increased still further using phage-display technology, with new libraries prepared from pre-existing antibody fragments by means of random (Hawkins et al., J. Mol. Biol. 226, 889 (1992); Gram et al., PNAS-USA 89, 3576 (1992)), codon-based (Glaser et al., J. Immunol. 149, 3903 (1992)) or site-directed mutagenesis (Balint & Larrick, Gene 137, 109 (1993), by shuffling the chains of individual domains with those of fragments from naive repertoires (Marks et al., Bio/Technol. 10, 779 (1992)) or by using bacterial mutator strains (Low et al., J. Mol. Biol. 260, 359 (1996)), and isolating antibody fragments having improved properties by reselecting under stringent conditions (Hawkins et al., J. Mol. Biol. 226, 889 (1992)). In addition, murine antibody fragments can be humanized by the step-wise replacement of one of the variable domains with a human repertoire and subsequent selection using the original antigen (guided selection) (Jespers et al., Bio/Technol. 12, 889 (1994)). Alternatively, murine antibodies are humanized by specifically replacing the hypervariable regions of human antibodies with the corresponding regions of the original murine antibody (Jones et al., Nature 321, 522 (1987)).

Consequently, within the meaning of the invention, the coupling substances basically include all substances which are able to penetrate into a cell. Within the meaning of this invention, particular preference is given to those coupling substances which are already used as pharmaceuticals independently of gene therapy.

For example, these coupling substances include the following coupling substances [component j)] together with the affiliated proteins which bind to the particular coupling substance and whose genes are to be inserted into components f) and h) in order to express the fusion proteins f) and h), respectively:

coupling substance: rapamycin or rapamycin analogues, such as L685818 (Becker et al., J. Biol. Chem. 268, 11335 (1993)), together with the following binding proteins (and their genes);
  the FK506-binding protein (FKBP; Bierer et al., Proc. Natl. Acad. Sci. USA 87, 9231, 1990))
  the FKBP/rapamycin-associated protein, which binds to the rapamycin/FKBP complex, or its part sequence which binds to the rapamycin/FKBP complex (FRAP; Brown et al., Nature 369, 756 (1994); Chiu et al., Proc. Natl. Acad. Sci. USA 91, 12574 (1994); Sabatini et al., Cell 78, 35 (1994); Sabers et al., J. Biol. Chem. 270, 815 (1995)).
  Instead of using genes for FKBP and FRAP, use can be made of genes for a recombinant Fv fragment which binds to rapamycin and/or inhibits the binding of FKBP or of FRAP to rapamycin.

Coupling substance: dimers (FK1012) of FK506 (Spencer et al., Science 262, 1019 (1993); Pruschy et al., Chem. Biol. 1, 163 (1994)) together with the following binding proteins (and their genes):
  the FK506-binding protein (FKBP, see above);
  calcineurin (Lin et al., Cell 66, 807 (1991)) or its part sequence which binds to the FK506 complex (Clipstone et al., J. Biol. Chem. 269, 26431 (1994)); and
  the gene for a recombinant Fv fragment which inhibits the binding of FK506 to calcineurin (Ho et al., Nature 382, 822 (1996)) and can be inserted in place of the calcineurin gene.

Coupling substance: dimers of cyclosporin A (Belshaw et al., Proc. Natl. Acad. Sci. USA 93, 4604 (1996)) together with the following binding proteins (and their genes):
  cyclophilin (Belshaw et al., Proc. Natl. Acad. Sci. USA 93, 4604 (1996));
  calcineurin or its part sequence which binds to the cyclosporin A/cyclophilin complex (see above); and
  the gene for a recombinant Fv fragment which inhibits the binding of cyclosporin A to cyclophilin can be inserted instead of the gene for cyclophilin.

Coupling substance: monomers of cyclosporin A together with the following binding proteins (and their genes):
  cyclophilin;
  gene for a recombinant Fv fragment which binds to cyclosporin A in the cyclophilin/cyclosporin A complex (Cacalano et al., Molec. Immunol. 29, 107 (1992));
  as an alternative to cyclophilin, use can be made of genes for different recombinant Fv fragments which bind to different epitopes of cyclosporin A (Vix et al., Proteins 15, 339 (1993); Cacalano et al., Mol. Immunol. 29, 107 (1992); Rauffer et al., Molec. Immunol. 31, 913 (1994)).

Coupling substance: methotrexate together with the following binding proteins (and their genes):
  antibodies or antibody fragments (recombinant Fv fragments) against methotrexate (Pimm et al., Brit. J. Cancer 61, 508 (1990); Kato et al., J. Immunol. Methods 67, 321 (1984));
  antibodies or antibody fragments (recombinant Fv fragments) against the pteridine group (Cot et al., Hybridoma 6, 87 (1987));
  antibodies or antibody fragments (recombinant Fv fragments) against the benzene group (Cot et al., Hybridoma 6, 87 (1987)); and
  dihydrofolate reductase (Masters et al., Gene 21, 59 (1983); Swift et al., Mol. Gen. Genetics 181, 441 (1981); Goldsmith et al., Mol. Cell Biol. 6, 878 (1986)).

Coupling substance: gentamycin together with the following binding proteins (and their genes):
  antibodies or antibody fragments (recombinant Fv fragments) against gentamycin (Sierra-Madero et al., J. Clin. Microbiol. 26, 1904 (1988)).

Coupling substance: ceftazidime together with the following binding proteins (and their genes):
  antibodies or antibody fragments (recombinant Fv fragments) against ceftazidime (Shimizu et al., Int. Arch. Allergy Immunol. 98, 392 (1992)).

Coupling substance: cephalexin together with the following binding proteins (and their genes):
  antibodies or antibody fragments (recombinant Fv fragments) against the acyl side chain at the C7 position of the cephem (Nagakura et al., Int. Arch. Allergy Applied Immunol. 93, 126 (1990)).

Coupling substance: folic acid together with the following binding proteins (and their genes):
  folic acid-binding protein (Ratnam et al., Biochem. 28, 8249 (1989); Elwood, J. Biol. Chem. 264, 14893 (1989); Sadasivan et al., Biochem. Biophys. Acta 1131, 91 (1992))
  antibodies or antibody fragments (recombinant Fv fragments) against folic acid (ayburn et al., Clin. Chem. 30, 1007 (1984)).

Coupling substance: retinoic acid together with the following binding proteins (and their genes):
  retinoic acid-binding domain of the cellular retinoic acid-binding protein (Stoner et al., Cancer Res. 49, 1497 (1989); Eller et al., Clin. Res. 39, 560A (1991)); and
  antibodies or antibody fragments (recombinant Fv fragments) against retinoic acid (Twal et al., Developm. Biol. 168, 225 (1995); Zhou et al., J. Immunol. Methods 138, 211 (1991)).

Coupling substance: penicillin together with the following binding proteins (and their genes):
  antibodies or antibody fragments (recombinant Fv fragments) against amoxicillin (Mayorga et al., Toxicol. 97, 225 (1995); Mayorga et al., Int. Arch. Allergy Applied Immunol. 99, 443 (1992));
  antibodies or antibody fragments (recombinant Fv fragments) against the benzylpenicilloyl group (de Haan et al., Int. Arch. Allergy Applied Immunol. 76, 42 (1985); Fukushima et al., Clin. Exp. Immun. 68, 427 (1987));
  antibodies or antibody fragments (recombinant Fv fragments) against penicillin (Sierra-Madero et al., J. Clin. Microbiol. 26, 1904 (1988)); and
  the penicillin-binding protein (Popham et al., J. Bacteriol. 177, 326 (1995); J. Bacteriol. 176, 7197 (1994)).

Coupling substance: 4-hydroxytamoxifen or tamoxifen together with the following binding proteins (and their genes):
  oestrogen-binding domain of the oestrogen receptor protein (Spreafico et al., Eur. J. Pharmacol. 227, 353 (1992); Green et al., Nature 320 (134 (1986)); and
  antibodies or antibody fragments (recombinant Fv fragments) against the oestrogen receptor/oestrogen or 4-hydroxytamoxifen complex (Giambiagi et al., J. Steroid Biochem. 30, 213 (1988); Biochim. Biophys. Acta 883, 559 (1986); Katzenellenbogen et al., Biochem. 26, 2364 (1987); Tate et al., Breast Cancer Res. Treatm. 3, 267 (1983)).

Coupling substance: tetracycline together with the following binding proteins (and their genes):
  the tetracycline repressor protein (Gossen et al., PNAS USA 89, 5547 (1992)); and
  antibodies and antibody fragments against tetracycline.

Coupling substance: conjugate of tetracycline and isopropyl-β-D-thiogalactoside together with the following binding proteins (and their genes):
  the tetracycline repressor protein (Gossen et al., PNAS USA 89, 5547 (1992)); and
  the lac repressor (lac I) protein (Brow et al., Cell 49, 603 (1987)).

In accordance with the invention, the genes for the coupling substance [component j)]-binding proteins A and B are linked
in fusion protein f) [component f), protein A], to the gene for the activation domain of a transcription factor protein, and
in fusion protein h) [component h), protein B], to the gene for a DNA-binding protein, with this DNA-binding protein being selected such that it binds specifically to the activation sequence [component i)] (see FIGS. 8 and 9). In this context, a "naturally occurring protein" is a protein that is found in nature. Thus, a binding domain that comes from a "naturally occurring protein" is distinct from a binding domain that has been designed by man. A naturally occuring protein is found and isolated from nature. The nucleic acid sequence information for a "binding domain" may be used separately or combined with other sequence information to form a binding domain from a naturally occurring protein.

Within the meaning of the invention, the following can be used, for example, as the nucleotide sequence for the activation domain in component f):
herpes virus VP16 transactivation domain (Greaves et al., J. Virol. 64, 2716 (1990); 65, 6705 (1991));
the p65 subunit of the NF-xB transcription factor protein (Schmitz et al., EMBO J. 10, 3805 (1991)); and
the Oct-2 N-terminal glutamine-rich domain which is directly or indirectly (e.g. by way of the Gal4-binding protein) linked to the Oct-2 C-terminal proline-rich Oct-2 domain (Tanaka et al., Mol. Cell Biol. 14, 6046 (1994)).

The following can, for example, be used as the nucleotide sequence for the DNA-binding protein in fusion protein h) [component h)] and as the affiliated activation sequence [component i)]:

Embodiment F), Comprising
1. a nucleotide sequence for the DNA-binding protein in fusion protein h), comprising:
    a cDNA for the DNA-binding domain of the Gal4 protein (amino acids 1 to 147; Chasman and Kornberg, Mol. Cell Biol. 10, 2916 (1990)) and, at its 3' end, the SV40 nuclear localization signal (NLS) (SV40 large T; amino acids 126 to 132: e.g. (SEQ ID NO:2) PKKKRKV; Dingwall et al., TIBS 16, 478 (1991)) and, at its 3' end, the HSV-1 VP16 acid transactivation domain (TAD) (amino acids 406 to 488; Triezenberg et al., Genes Developm. 2, 718 (1988); Triezenberg, Curr. Opin. Gen. Developm. 5, 190 (1995)), and
2. the affiliated activation sequence (SEQ ID NO:1) [component i)], comprising:
    at least one sequence [e.g. nucleotide sequence 5'-CGGACAACTGTTGACCC-3'] for binding the Gal4 protein (Chasman and Kornberg, Mol. Cell Biol. 10, 2916 (1989)) and, at its 3' end,
    the SV40 basal promoter (nucleic acids 48 to 5191; Tooze (ed.), DNA Tumor Viruses (Cold Spring Harbor N.Y., New York; Cold Spring Harbor Laboratory), or
    the c-fos promoter (Das et al., Nature 374, 657 (1995)) and, at its 3' end, the HSV1 VP16 acid transactivation domain (TAD) (amino acids 406 to 488; Triezenberg et al., Genes Developm. 2, 718 (1988); Triezenberg, Curr. Opin. Gen. Developm. 5, 190 (1995)), or
    the U2 sn RNA promoter and, at its 3' end, the HSV1-VP16 TAD or at least a sequence of the Oct-2 activation domain (amino acids 438 to 479; Tanaka et al., Mol. Cell Biol. 14, 6046 (1994); Das et al., Nature 374, 657 (1995)), or
    the HSV promoter (Papavassiliou et al., J. Biol. chem. 265, 9402 (1990); Park et al., Molec. Endocrinol. 7, 319 (1993)), or
    any other promoter which can be activated non-specifically, cell-specifically, virus-specifically and/or cell cycle-specifically.

Embodiment G), Comprising
1. a nucleotide sequence for the DNA-binding protein in fusion protein h), comprising:
    the cDNA for the DNA-binding domain of the LexA protein (amino acids 1 to 81; Kim et al., Science 255, 203 (1992)) or the entire LexA protein (amino acids 1 to 202; Brent et al., Cell 43, 729 (1985)) and, at its 3' end, the SV40 nuclear localization signal (NLS) (SV40 large T; amino acids 126 to 132: e.g. (SEQ ID NO:2) PKKKRKV; Dingwall et al., TIBS 16, 478 (1991)) and, at its 3' end, the HSV-1 VP16 acid transactivation domains (TAD) (amino acids 406 to 488; Triezenberg et al., Genes Developm. 2, 718 (1988); Triezenberg, Curr. Opin. Gen. Developm. 5, 190 (1995)) and 2. the affiliated activation sequence [component i)]:
   the sequence (SEQ ID NO:3) [e.g. nucleotide sequence 5'-TACTGTATGTACATACAGTA-3'] for binding the LexA protein (LexA operator, Brent et al., Nature 612, 312 (1984)], to whose 3' end
   the SV40 basal promoter (nucleic acids 48 to 5191; Tooze (ed.), DNA Tumor Viruses (Cold Spring Harbor N.Y., New York; Cold Spring Harbor Laboratory) or another promoter (see Embodiment F) is attached.

Embodiment H), Comprising 1 the nucleotide sequence for the DNA-binding protein in fusion protein h), comprising
   the cDNA for the lac repressor (lac I) protein (Brown et al., Cell 49, 603 (1987); Fuerst et al., PNAS USA 86, 2549 (1989)) and, at its 3' end, the SV40 nuclear localization signal (NLS) (SV40 large T; amino acids 126–132; e.g. (SEQ ID NO:2) PKKKRKV; Dingwall et al., TIBS 16, 478 (1991)) and, at its 3' end, the HSV-1 VP16 acid transactivation domain (TAD) (amino acids: 406–488; Triezenberg et al., Genes Developm. 2, 718 (1988); Triezenberg, Curr. Opin. Gen. Developm. 5, 190 (1995)), and 2. the affiliated activation sequence [component i)]
   containing at least a lac operator sequences (SEQ ID NO:4) (e.g. nucleotide sequence: 5'-GAATTGTGAGCGCTCACAATTC-3') for binding the lac I repressor protein (Fuerst et al., PNAS USA 86, 2549 (1989); Simons et al., PNAS USA 81, 1624 (1984)) and, at its 3'end, the SV40 basal promoter (nucleic acids 48 to 5191; Tooze (ed.) DNA Tumor Viruses (Cold Spring Harbor New York, N.Y., Cold Spring Harbor Laboratory) or another promoter (see Embodiment F).

Embodiment I), Comprising 1. a nucleotide sequence for the DNA-binding protein in fusion protein h), comprising
   the cDNA for the tetracycline repressor (tet R) protein (Gossen et al., PNAS USA 89, 5547 (1992); Dingermann et al., EMBO J. 11, 1487 (1992)) and, at its 3' end, the SV40 nuclear localization signal (NLS) (SV40 large T; amino acids 126–132; e.g. (SEQ ID NO:2) PKKKRKV; Dingwall et al., TIBS 16, 478 (1991)) and, at its 3' end, the HSV-1 VP16 acid transactivation domain (TAD) (amino acids: 405–488; Triezenberg et al., Genes Developm. 2, 718 (1988); Triezenberg, Curr. Opin. Gen. Developm. 5, 190 (1995)), and 2. the affiliated activation sequence [component i)]
   containing at least a tetracyclin operator (tet O) sequence (SEQ ID NO:5) (e.g. nucleotide sequence: 5'-TCGAGTTTACCACTCCCTATCAGTGATAGAG AAAAGTGAA AG-3') for binding the tetracycline repressor (tet R) protein and, at its 3' end,
   the basal SV40 promoter (nucleic acids 48 to 5191; Tooze (ed.) DNA Tumor Viruses (Cold Spring Harbor New York, N.Y., Cold Spring Harbor Laboratory) or another promoter (see Embodiment F).

Embodiment J), Comprising 1. a nucleotide sequence for the DNA-binding protein in fusion protein h), comprising:
   the cDNA for the ZFHD1 protein (Pomerantz et al., Science 267, 93 (1995)) and, at its 3' end, the SV40 nuclear localization signal (NLS) (SV40 large T; amino acids 126 to 132; e.g. (SEQ ID NO:2) PKKKRKV; Dingwall et al., TIBS 16, 478 (1991)) and, at its 3' end, the HSV-1 VP16 acid transactivation domain (TAD) (amino acids 406 to 488; Triezenberg et al., Genes Developm. 2, 718 (1988); Triezenberg, Curr. Opin. gen. Developm. 5, 190 (1995)), and 2. the affiliated activation sequence [component i)], comprising:
   at least one sequence (SEQ ID NO:6) [e.g. nucleotide sequence 5'-TAATGATGGGCG-3'] for binding the ZFHD-1 protein (Pomerantz et al., Science 267, 93 (1995)) and, at its 3' end, the basal SV40 promoter (nucleic acids 48 to 5191; Tooze (ed.), DNA Tumor Viruses (Cold Spring Harbor New York, N.Y.; Cold Spring Harbor Laboratory) or another promoter (see possibility F).

3) Promoter Sequences

Within the meaning of the invention, nucleotide sequences which, after binding transcription factor proteins, activate the transcription of a structural gene which is located in an adjacent position at the 3' end, are used as promoter sequences [components b), e), g) and i)]. The choice of the promoter sequences depends on the disease treated and on the target cell transduced. Thus, promoter sequence can be activated in an unrestricted manner, in a target cell-specific manner, under particular metabolic conditions, in a cell cycle-specific manner or in a virus-specific manner. Furthermore, identical or different promoter sequences can be employed in components b), e) and/or g) and in component i). Examples of these promoter sequences, in addition to the promoter sequences which have already been cited in Embodiments A) to J), are:

promoters and activator sequences which can be activated in an unrestricted manner the RNA polymerase III promoter the RNA polymerase II promoter the CMV promoter and CMV enhancer the SV40 promoter viral promoter sequences and activator sequences, such as

HBV

HCV

HSV

EBV

HTLV

HIV

When the HIV promoter is used, the entire LTR sequence including the TAR sequence (position $\leq -453$ to $\geq +80$, Rosen et al., Cell 41, 813 (1985) is employed as the virus-specific promoter.

Promoter sequences or enhancer sequences which can be activated metabolically, such as an enhancer or promoter which is inducible by hypoxia.

Promoters which can be activated in a cell cycle-specific manner, such as the cdc25C gene promoter, the cyclin A gene promoter, the cdc2 gene promoter, the B-myb gene promoter, the DHFR gene promoter or the E2F-1 promoter, or else binding sequences for transcription factor proteins which appear or are activated during cell proliferation. These binding sequences include, for example, binding sequences for c-myc-proteins. These binding sequences also include monomers or multimers of the nucleotide sequence which is termed a myc E box, e.g. (SEQ ID NO: 7) [5'-GGAAGCAGAC-CACGTGGTCTGCTTCC-3', Blackwood and Eisenmann, Science 251, 1211, (1991)].

Promoters which can be activated by tetracycline, such as the tetracycline operator in combination with a corresponding repressor.

Chimeric promoters.

A chimeric promoter constitutes the combination of an upstream activator sequence, which can be activated cell-specifically, metabolically or virus-specifically, with a downstream promoter module which can bind the transcription factor proteins of the CDF and CHF or E2F and CHF families and is thereby able to inhibit activation of the upstream activator sequence in the G0 and G1 phases of the cell cycle.

Hybrid promoters, for example in the form in which the TATA box of a promoter is mutated, with this mutation being offset by a corresponding mutation in the gene of a TATA-binding protein and this TATA-binding protein being under the control of a further promoter.

Promoters which can be activated in a cell-specific manner.

These promoters preferably include promoters or activator sequences from genes which preferably encode proteins in selected cells.

For example, within the meaning of the invention, use is preferably to be made of promoters for the following proteins in the following cells:

Promoter sequences or activator sequences which are activated in endothelial cells brain-specific, endothelial glucose-1-transporter endoglin VEGF receptor 1 (flt-1)

VEGF receptor 2 (flk-1, KDR)

til-1 or til-2

B61 receptor (Eck receptor)

B61 endothelin, especially endothelin B endothelin-1 endothelin receptors, in particular the endothelin B receptor

IL-1α, IL-1β

IL-1 receptor vascular cell adhesion molecule (VCAM-1)

synthetic activator sequences

As an alternative to natural endothelial-specific promoters, use can also be made of synthetic activator sequences which comprise oligomerized binding sites for transcription factor proteins which are preferentially or selectively active in endothelial cells. An example of these transcription factor proteins is the transcription factor protein GATA-2, whose binding site in the endothelin-1 gene, for example, is 5'-TTATCT-3'.

Promoters or activator sequences which are activated in cells in the vicinity of activated endothelial cells

VEGF

The gene-regulatory sequences for the VEGF gene are the 5' flanking region, or the 3' flanking region, or the c-Src gene, or the v-Scr gene Steroid hormone receptors and their promoter elements (Truss and Beato, Endocr. Rev. 14, 459 (1993)), in particular the mouse mammary tumour virus promoter Promoters or activator sequences which are activated in muscle cells, in particular smooth muscle cells tropomyosin α-actin α-myosin receptor for PDGF receptor for FGF

MRF-4 phosphofructokinase A phosphoglycerate mutase troponin C myogenin receptors for endothelin A desmin

VEGF

The gene-regulatory sequences for the VEGF gene have already been listed in the section entitled "Promoters which are activated in cells in the vicinity of activated endothelial cells" (see above).

"Artificial" promoters

Factors of the helix-loop-helix (HLH) family (MyoD, Myf-5, myogens and MRF4) are reported to be muscle-specific transcription activators. The muscle-specific transcription activators also include the zinc finger protein GATA-4 and the MEF transcription factor groups.

The HLH proteins, and also GATA-4, exhibit muscle-specific transcription not only with promoters of muscle-specific genes but also in a heterologous context, that is with artificial promoters as well. Examples of these artificial promoters are:

multiple copies of the DNA site for binding muscle-specific HLH proteins, such as the E box (Myo D) (SEQ ID NO:8) (e.g. 4×AGCAGGTGTTGGGAGGC)

multiple copies of the DNA site for binding GATA-4 of the α-myosin heavy chain genes (SEQ ID NO: 9) (e.g. 5'-GGCCGATGGGCAGATA-GAGGGGGCCGATGGGCAGATAGAGG3')

Promoters and activator sequences which are activated in glia cells These include, in particular, gene-regulatory sequences or elements, respectively, from genes which, for example, encode the following proteins:

the Schwann cell-specific protein periaxin glutamine synthetase the glia cell-specific protein (glial fibrillary acidic protein=GFAP)

the glia cell protein S100b

IL-6 (CNTF)

5-HT receptors

TNFα

IL-10 insulin-like growth factor receptor I and II VEGF

The gene-regulatory sequences for the VEGF gene have already been listed above.

Promoters and activator sequences which are activated in haematopoietic cells

These gene-regulatory sequences include promoter sequences for genes for a cytokine or its receptor, which genes are expressed in haematopoietic cells or in adjacent cells such as the stroma.

These sequences include promoter sequences for, by way of example, the following cytokines and their receptors:

stem cell factor receptor stem cell factor

IL-1α

IL-1 receptor

IL-3

IL-3 receptor (αsubunit)
IL-3 receptor (βsubunit)
IL-6
IL-6 receptor
GM-CSF
GM-CSF receptor (αchain)
interferon regulatory factor 1 (IRF-1)
The promoter of IRF-1 is activated to the same extent by IL-6 as by IFN-α, IFN-β or IFN-γ.
erythropoietin
erythropoietin receptor Promoters and activator sequences which are activated in lymphocytes and/or macrophages
These include, for example, the promoter sequences and activator sequences of the genes for cytokines, cytokine receptors and adhesion molecules and receptors for the Fc fragment of antibodies.
Examples of these latter are:
IL-1 receptor
IL-1α
IL-1β
IL-2
IL-2 receptor
IL-3
IL-3 receptor (αsubunit)
IL-3-receptor (βsubunit)
IL-4
IL-4 receptor
IL-5
IL-6
interferon regulatory factor 1 (IRF-1)
(The promoter of IRF-1 is activated to the same extent by IL-6 as by IFN-α or IFN-β).
IFN-γ-responsive promoter
IL-7
IL-8
IL-10
IL-11
IFN-γ
GM-CSF
GM-CSF receptor (αchain)
IL-13
LIF
macrophage colony stimulating factor (M-CSF) receptor
type I and II scavenger macrophage receptors
MAC-1 (leukocyte function antigen)
LFA-1α (leukocyte function antigen)
p150,95 (leukocyte function antigen)

Promoter sequences and activator sequences which are activated in synovial cells
These include the promoter sequences for matrix metalloproteinases (MMP), for example for
MMP-1 (interstitial collagenase)
MMP-3 (stroma lysin/transin)
These furthermore include the promoter sequences for tissue inhibitors of metalloproteinases (TIMP), for example
TIMP-1
TIMP-2
TIMP-3

Promoters and activator sequences which are activated in leukaemia cells
These include, for example, promoters for
c-myc
HSP-70
bcl-1/cyclin D-1
bcl-2
IL-6
11-10
NFα, TNFβ
HOX-11
BCR-Abl
E2A-PBX-1
PML-RARA
(promyelocytic leukaemia—retinoic acid receptor)
c-myc
c-myc proteins bind to, and activate, multimers of the nucleotide sequence which is termed the myc E box (SEQ ID NO:7) (e.g. 5'-GGAAGCAGACCACGTGGTCTGCTTCC-3')

Promoters or activator sequences for tumour cells
A gene-regulatory nucleotide sequence with which transcription factor proteins, which are formed or are active in tumour cells, interact is envisaged as the promoter sequence or activator sequence.

Within the meaning of this invention, the preferred promoters or activator sequences include gene-regulatory sequences or elements, respectively, from genes which encode proteins which are formed, in particular, in cancer cells or sarcoma cells. Thus, in the case of small-cell bronchial carcinomas, preference is given to using the promoter of the N-CAM protein, in the case of ovarian carcinomas to using the promoter of the hepatitis growth factor receptor or of L-plastin, and in the case of pancreatic carcinomas to using the promoter of L-plastin or of polymorphic epithelial mucin (PEM).

4) Nuclear Export Signals and Nuclear Export Factors

Within the meaning of the invention, nuclear export signals (NES) are preferably the retroviral rev-responsive element (RRE) sequences. In the case of HIV-1, this RRE is a sequence of 243 nucleotides (nucleotides 7362–7595; Muesing et al., Nature 313, 450 (1985)) in the env gene (Malim et al., Nature 338, 254 (1989); Kjems et al., PNAS 88, 683 (1991)). However, within the meaning of the invention, the nuclear export signal (NES) can also be any homologous and/or functionally similar (analogous) nucleotide sequence such as, for example, the HBV virus RRE-equivalent element (Huang et al., Mol. Cell Biol. 13, 7476 (1993)).

In the novel nucleic acid constructs, the nuclear export factor (NEF) is a nucleotide sequence which encodes a protein which binds to the mRNA of the NRS and mediates transport of the NRS-containing premessenger RNA or messenger RNA out of the cell nucleus and into the cytoplasm (or out of the cytoplasm and into the cell nucleus). Within the meaning of the invention, use is made, in particular, of the rev gene from retroviruses, especially from the HIV-1 or HIV-2 virus (Daly et al., Nature 342, 816 (1989); Emerman et al., Cell 57, 1155 (1989); Felber et al., PNAS 86, 1495 (1989); Fischer et al., EMBO J. 13, 4105 (1994)).

The rev protein of the retroviral rev gene binds, by its N-terminal domain (Zapp et al., Nature 342, 7154 (1989); Malim et al., Cell 65, 241 (1991)) to the RRE in the pre-mRNA (Iwai et al., Nucl. Acids Rex. 20, 6465 (1992)). The binding between the RRE and the rev protein facilitates transport of non-spliced premessenger RNA, and also of any other RNA which contains an RRE, out of the cell nucleus and into the cytoplasm (Fischer et al., EMBO J. 13, 4105 (1994); Fischer et al., Cell 82, 475 (1995)) and thereby enhances translation substantially.

Within the meaning of the invention, use can also be made, as NEF, of nucleotide sequences which encode proteins which are homologous, and functionally similar, to the HIV-1 rev protein (Bogerd et al., Cell 82, 485 (1995)), such as the visna-maedi virus (VMV; Tiley et al., J. Virol. 65, 3877 (1991)) rev gene or the caprine arthritis encephalitis virus (CAEV; Tiley et al., J. Virol. 65, 3877 (1991)) rev gene.

However, within the meaning of the invention, use can also be made of those genes which encode proteins which, while only possessing slight, or no, homology with the rev protein are functionally similar to the HIV-1 rev protein.

These genes include, for example, the HTLV-1 rev gene (Cullen, Microbiol. Rev. 56, 375 (1992)) and the rev gene of the equine infectious anaemia virus (EIAV) and of the feline immunodeficiency virus (FIV) (Manusco et al., J. Virol. 68, 1988 (1994)).

In an alternative embodiment, the NEFs can also be nucleotide sequences for proteins which effect secretion of RNA out of the nucleus even without this RNA being retained in the nucleus by means of an NRS. These proteins include, for example, the transcription factor protein TFIIIA (Gaddat et al., Cell 60, 619 (1990); Drew et al., Gene 159, 215 (1995)) or the heterogeneous nuclear ribonucleoprotein A1 (hnRNPA1 protein; Pinol-Roma et al., Nature 355, 730 (1992)).

In a broader sense, the nuclear transport proteins also include heat shock protein 70 (hsp70; Mandell et al., J. Cell Biol. 111, 1775 (1990)) or the protein kinase inhibitor CPKI (Fantozzi et al., J. Biol. Chem. 269, 2676 (1994); Wen et al., J. Biol. Chem. 269, 32214 (1994)).

Features possessed in common by the NEF and its homologous and analogous proteins are the presence of a more aminoterminally located domain for binding the monomeric protein to the NRS RNA (J. Virol. 64, 881 (1990); Kjems et al., EMBO J. 11, 119 (1992)) and a domain which is usually leucine-rich (hnRnPA1 is an exception to this) and which is necessary for the transport function of the NEF (Wen et al., Cell 82, 463 (1995); Fischer et al., Cell 82, 475 (1995); Malim et al., J. virol. 65, 4248 (1991); Venkatesh et al., Virol. 178, 327 (1990)).

Within the meaning of this invention, expression of the NEF gene is under the control of a promoter sequence [component b''')] which is located upstream at the 5' end of the NEF gene (see FIGS. 2 and 7, and as already described above) or of the pharmacologically controllable promoter module (see FIGS. 8 and 9).

5) Internal Ribosome Entry Site (IRES)

An internal ribosome entry site makes it possible to express two DNA sequences which are linked to each other ("mutually linked") by way of an IRES.

IRESs of this nature have been described, for example, by Montford and Smith TIG 11, 179 (1995); Kaufman et al., Nucl. Acids Res. 19, 4485 (1991); Morgan et al., Nucl. Acids Res. 20, 1293 (1992); Dirks et al., Gene 128, 247 (1993); Pelletier and Sonenberg, Nature 334, 320 (1988) and Sugitomo et al., BioTechn. 12, 694 (1994).

Thus, for example, the cDNA of the poliovirus IRES sequence (position $\leq 140$ to $\geq 630$ of the 5' UTR (Pelletier and Sonenberg, Nature 334, 320 (1988)) can be used to link the DNA of component c) to the DNA of component d).

6) Structural Genes

Within the meaning of the invention, the structural genes [component c)] encode an active compound for the prophylaxis and/or therapy of a disease. Structural genes and promoter sequences are to be selected with regard to the nature of the therapy of the disease and taking into account the target cell to be transduced.

For example, the following combinations of promoter sequences (examples, see Section 3) and structural genes are to be selected in association with the following diseases:

a) Therapy of Tumours

Target cells:
- proliferating endothelial cells, or
- stroma cells and muscle cells which are adjacent to the endothelial cell, or
- tumour cells or leukaemia cells Promoters:
- endothelial cell-specific and cell cycle-specific, or
- cell non-specific or muscle cell-specific and cell cycle-specific, or
- tumour cell-specific (solid tumours and leukaemias)

Structural genes for inhibitors of cell proliferation, for example for
- the retinoblastoma protein (pRb=p110) or the related p107 and p130 proteins
- the p53 protein
- the p21 (WAF-1) protein
- the p16 protein
- other cdk inhibitors
- the GADD45 protein
- the bak protein.

The retinoblastoma protein (pRb/p110) and the related p107 and p130 proteins are inactivated by phosphorylation. Preference is given to using such genes for these cell cycle inhibitors which exhibit mutations for the inactivation sites of the expressed proteins without the function of these proteins thereby being impaired. Examples of these mutations have been described in the case of p110. The DNA sequence for the p107 protein or the p130 protein is mutated in an analogous manner.

In the cell, the p53 protein is inactivated either by binding to special proteins, such as MDM2, or by oligomerization of the p53 by way of the dephosphorylated C-terminal serine 392. Preference is therefore given to using a DNA sequence for a p53 protein which has been truncated at the C terminus by removing the serine 392.

Structural genes for coagulation-inducing factors and angiogenesis inhibitors, for example;
- plasminogen activator inhibitor-1 (PAI-1)
- PAI-2
- PAI-3
- angiostatin
- interferons, in particular
  - IFNα
  - IFNβ
  - IFNγ
- platelet factor 4
- IL-12
- TIMP-1
- TIMP-2
- TIMP-3
- leukaemia inhibitory factor (LIF)
- tissue factor (TF) and its coagulation-active fragments Structural genes for cytostatic and cytotoxic proteins, for example for
  perforin
  granzyme
  IL-2
  IL-4
  IL-12
  interferons, such as
    IFNα
    IFNβ
    IFNγ
  TNF, in particular
    TNFα
    TNFβ
  oncostatin M
  sphingomyelinase
  magainin and magainin derivatives
Structural genes for cytostatic or cytotoxic antibodies and for fusion proteins between antigen-binding antibody fragments and cytostatic, cytotoxic or inflammation-inducing proteins or enzymes
  The cytostatic or cytotoxic antibodies include those which are directed against membrane structures of endothelial cells, as have been described, for example, by Burrows et al. (Pharmac. Ther. 64, 155 (1994)), Hughes et al., (Cancer Res. 49, 6214 (1989)) and Maruyama et al., (PNAS USA 87, 5744 (1990)). These antibodies include, in particular, antibodies against the VEGF receptors.
  These antibodies furthermore include cytostatic or cytotoxic antibodies which are directed against membrane structures on tumour cells. Antibodies of this nature have been reviewed, for example, by Sedlacek et al., Contrib. to Oncol. 32, Karger Verlag, Munich (1988) and Contrib. to Oncol. 43, Karger Verlag, Munich (1992). Other examples are antibodies against:
    sialyl Lewis
    peptides on tumours which are recognized by T cells
    proteins which are expressed by oncogenes
    gangliosides such as GD3, GD2, GM2, 9-0-acetyl GD3, fucosyl GM1
    blood group antigens and their precursors
    antigens on polymorphic epithelial mucin
    antigens on heat shock proteins
  These antibodies furthermore include antibodies which are directed against membrane structures of leukaemia cells. A large number of monoclonal antibodies of this nature have already been described for diagnostic and therapeutic methods (reviews in Kristensen, Danish Medical Bulletin 41, 52 (1994); Schranz, Therapia Hungarica 38, 3 (1990); Drexler et al., Leuk. Res. 10, 279 (1986); Naeim, Dis. Markers 7, 1 (1989); Stickney et al., Curr. Opin. Oncol. 4, 847 (1992); Drexler et al., Blut 57, 327 (1988); Freedman et al., Cancer Invest. 9, 69 (1991)). Depending on the type of leukaemia, the following monoclonal antibodies, or their antigen-binding antibody fragments, are, for example, suitable for use as ligands:

| Cells | Membrane antigen | Monoclonal antibodies described by |
|---|---|---|
| AML | CD13 | Kaneko et al., Leuk. Lymph. 14, 219 (1994) |
|  | CD14 | Ball, Bone Marrow Transplant. 3, 387 (1988) |
|  | CD15 | Campos et al., Eur. J. Cancer 28, 37 (1992) |
|  | CD33 | Jurcic et al., Leukaemia 9, 244 (1995) |
|  | CAMAL | Shellard et al., Exp. Hematol. 19, 136 (1991) |
|  | Sialosyl-Le | Muroi et al., Blood 79, 713 (1992) |
| B-CLL | CD5 | Tassone et al., Immunol. Lett. 39, 137 (1994) |
|  | CD1c | Orazi et al., Eur. J. Haematol. 47, 28 (1991) |
|  | CD23 |  |
|  | Idiotypes and isotypes of the membrane immunoglobulins | Schroeder et al., Immunol. Today 15, 289 (1994) |
| T-CLL | CD33 | Imai et al., J. Immunol. 151, 6470 (1993) |
|  | M38 |  |
|  | IL-2-receptors | Waldmann et al., Blood 82, 1701 (1993) |
|  | T cell receptors |  |
| ALL | CALLA | Morishima et al., Bone Marrow Transplant. 11, 255 (1993) |
|  | CD19 | Anderson et al., Blood 80, 84 (1993) |
|  | Non-Hodgkin lymphoma | Okazaki et al., Blood 80, 84 (1993) |

The humanization of murine antibodies, and the preparation and optimization of the genes for Fab and recombinant Fv fragments are effected in analogy with the methods, which have already been described, for preparing recombinant Fv fragments (see Section 2). The recombinant Fv fragments are fused with genes for cytostatic, cytotoxic or inflammation-inducing proteins or enzymes in accordance with the state of the art which is known to the skilled person.
Structural genes for fusion proteins between target cell-binding ligands and cytostatic and cytotoxic proteins.
  These include all substances which bind to membrane structures or membrane receptors on endothelial cells. For example, they include IL-1 or growth factors, or their fragments or part sequences thereof, which bind to receptors which are expressed by endothelial cells, such as PDGF, bFGF, VEGF and TGFβ (Pusztain et al., J. Pathol. 169, 191 (1993)).
  They furthermore include adhesion molecules which bind to activated and/or proliferating endothelial cells. Adhesion molecules of this nature, such as Slex, LFA-1, MAC-1, LECAM-1, VLA-4 or vitronectin, have already been described (reviews in Augustin-Voss et al., J. Cell Biol. 119 483 (1992), Pauli et al., Cancer Metast. Rev. 9, 175 (1990), Honn et al., Cancer Metast. Rev. 11, 353 (1992) and Varner et al., Cell Adh. Commun. 3, 367 (1995)).
  They furthermore include substances which bind to membrane structures or membrane receptors of tumour cells or leukaemia cells. For example, they include growth factors, or their fragments or part sequences thereof, which bind to receptors which are expressed by leukaemia cells or tumour cells.
  Growth factors of this nature have already been described (reviews in Cross et al., Cell 64, 271 (1991), Aulitzky et al., Drugs 48, 667 (1994), Moore, Clin. Cancer Res. 1, 3 (1995) and Van Kooten et al., Leuk. Lymph. 12, 27 (1993)).
  The genes for these ligands which bind to the target cell are fused with genes for cytostatic, cytotoxic or inflammation-inducing proteins or enzymes in accordance with the state of the art using the methods which are known to the skilled person.

Structural genes for inducers of inflammations, for example for

RANTES (MCP-2)

monocyte chemotactic and activating factor (MCAF)

IL-8 macrophage inflammatory protein-1 (MIP-1α, -β)

neutrophil activating protein-2 (NAP-2)

IL-3

IL-5 human leukaemia inhibitory factor (LIF)

IL-7

IL-11

IL-13

GM-CSF

G-CSF

M-CSF cobra venom factor (CVF), or part sequences of CVF, which correspond functionally to human complement factor C3b, i.e. which are able to bind to complement factor B and which constitute a C3 convertase following cleavage by factor D.

human complement factor C3 or its part sequence C3b.

cleavage products of human complement factor C3 which resemble CVF functionally and structurally.

bacterial proteins which activate complement or elicit inflammations, such as Salmonella typhimurium porins, Staphylococcus aureus clumping factors, modulins, particularly those of Gram-negative bacteria, major outer membrane protein of legionellas or of Haemophilus influenza type B or of klebsiellas, or M molecules of group G streptococci.

Structural genes for enzymes for activating precursors of cytostatic agents, for example for enzymes which cleave inactive precursor substances (prodrugs) thereby forming active cytostatic agents (drugs).

Substances of this nature, and the prodrugs and drugs with which they are affiliated in each case, have already been reviewed by Deonarain et al. (Br. J. Cancer 70, 786 (1994)), by Mullen (Pharmac. Ther. 63, 199 (1994)) and by Harris et al. (Gene Ther. 1, 170 (1994)). For example, the DNA sequence for one of the following enzymes is to be used:

herpes simplex virus thymidine kinase varicella zoster virus thymidine kinase bacterial nitroreductase bacterial β-glucuronidase plant β-glucuronidase from Secale cereale human β-glucuronidase human carboxypeptidase (CB), for example
   mast cell CB-A
   pancreatic CB-B
   bacterial carboxypeptidase
   bacterial β-lactamase
   bacterial cytosine deaminase
   human catalase or peroxidase phosphatase, in particular
   human alkaline phosphatase
   human acid prostate phosphatase
   type 5 acid phosphatase oxidase, in particular
   human lysyl oxidase
   human acid D-aminooxidase peroxidase, in particular
   human glutathione peroxidase
   human eosinophilic peroxidase
   human thyroid peroxidase β-galactosidase b) Therapy of Autoimmune Diseases and Inflammations Target cells:
   proliferating endothelial cells, or
   macrophages and/or lymphocytes, or
   synovial cells Promoters:
   endothelial cell-specific and cell cycle-specific, or
   macrophage-specific and/or lymphocyte-specific and/or cell cycle-specific
   synovial cell-specific and/or cell cycle-specific Structural genes for the therapy of allergies, for example for

IFN-β

IFN-γ

IL-10 antibodies or antibody fragments against IL-4 soluble IL-4 receptors

IL-12

TGFβ

Structural genes for preventing the rejection of transplanted organs, for example for

IL-10

TGFβ soluble IL-1 receptors soluble IL-2 receptors

IL-1 receptor antagonists soluble IL-6 receptors immunosuppressive antibodies or their $V_H$- and $V_L$-containing fragments, or their $V_H$ and $V_L$ fragments which are connected by way of a linker, which are prepared, for example, in accordance with the method described by Marasco et al. (Proc. Natl. Acad. Sci. USA 90, 7889 (1993)). Examples of immunosuppressive antibodies are antibodies
   which are specific for the T cell receptor or its CD3 complex
   which are directed against CD4 or CD8, and furthermore
   which are directed against the IL-2 receptor, the IL-1 receptor or the IL-4 receptor, or
   which are directed against the adhesion molecules CD2, LFA-1, CD28 or CD40.

Structural genes for the therapy of antibody-mediated autoimmune diseases, for example for

TFGβ

IFN-α

IFN-β

IFN-γ

IL-12 soluble IL-4 receptors soluble IL-6 receptors immunosuppressive antibodies or their $V_H$- and $V_L$-containing fragments Structural genes for the therapy of cell-mediated autoimmune diseases, for example for

IL-6

IL-9

IL-10
IL-13
TNFα
IL-4
TNFβ
an immunosuppressive antibody or its $V_H$- and $V_L$-containing fragments Structural genes for inhibitors of cell proliferation, cytostatic or cytotoxic proteins and enzymes for activating precursors of cytostatic agents.

Examples of genes encoding proteins of this nature have already been cited in the section entitled "Structural genes for the therapy of tumours".

Within the meaning of the invention, use can be made, in the same form as already described at that point, of structural genes which encode fusion proteins which comprise antibodies, or Fab fragments or recombinant Fv fragments of these antibodies, or other ligands, which are specific for the target cell, and the abovementioned cytokines, growth factors, receptors, cytostatic or cytotoxic proteins and enzymes.

Structural genes for the therapy of arthritis

Within the meaning of the invention, structural genes are selected whose expressed protein directly or indirectly inhibits inflammation, for example in a joint, and/or promotes the reconstitution of extracellular matrix (cartilage and connective tissue) in the joint.

Examples of these proteins are
   IL-1 receptor antagonist (IL-1-RA);
      IL-1-RA inhibits the binding of IL-1α and IL-1β
   soluble IL-1 receptor;
      soluble IL-1 receptor binds and inactivates IL-1
   IL-6;
      IL-6 increases the secretion of TIMP and superoxides, and decreases the secretion of IL-1 and TNFα, by synovial cells and chondrocytes
   soluble TNF receptor;
      soluble TNF receptor binds and inactivates TNF.
   IL-4;
      IL-4 inhibits the formation and secretion of IL-1, TNFα and MMP
   IL-10;
      IL-10 inhibits the formation and secretion of IL-1, TNFα and MMP and increases the secretion of TIMP
   insulin-like growth factor (IGF-1)
      IGF-1 stimulates the synthesis of extracellular matrix.
   TGFβ, especially TGFβ1 and TGFβ2
      TGFβ stimulates the synthesis of extracellular matrix
   superoxide dismutase
   TIMP (tissue inhibitors of metalloproteinases) especially
      TIMP-1
      TIMP-2
      TIMP-3 c) Therapy of Deficient Haematopoiesis
Target cells:
   proliferating, immature cells of the haematopoietic system, or
   stroma cells which are located adjacent to the haematopoietic cells
Promoters:
   specific for haematopoietic cells and/or cell cycle-specific
   cell non-specific
Structural genes for the therapy of anaemia, for example for
   erythropoietin
Structural genes for the therapy of leucopenia, for example for
   G-CSF
   GM-CSF
Structural genes for the therapy of thrombocytopenia, for example for
   IL-3
   leukaemia inhibitory factor (LIF)
   IL-11
   thrombopoietin d) Therapy of Nervous System Damage
Target cells:
   glia cells, or
   proliferating endothelial cells
Promoters:
   glia cell-specific, or
   endothelial cell-specific and cell cycle-specific, or
   non-specific and cell cycle-specific
Structural genes for neuronal growth factors, for example
   FGF
   nerve growth factor (NGF)
   brain-derived neurotrophic factor (BDNF)
   neurotrophin-3 (NT-3)
   neurotrophin4 (NT4)
   ciliary neurotrophic factor (CNTF) p0 Structural genes for enzymes, for example for
   tyrosine hydroxylase
   dopa decarboxylase
Structural genes for cytokines and their inhibitors which inhibit or neutralize the neurotoxic effect of TNFα, for example for
   TGFβ
   soluble TNF receptors TNF receptors neutralize TNFα
   IL-10; IL-10 inhibits the formation of IFN gamma, TNFα, IL-2 and IL-4
   soluble IL-1 receptors
   IL-1 receptor I
   IL-1 receptor II Soluble IL-1 receptors neutralize the activity of IL-1
   IL-1 receptor antagonist
   soluble IL-6 receptors e) Therapy of Disturbances of the Blood Coagulation System and the Blood Circulation System
Target cells:
   endothelial cells, or
   proliferating endothelial cells, or
   somatic cells in the vicinity of endothelial cells and smooth muscle cells, or
   macrophages
Promoters:
   cell non-specific, or
   cell non-specific and cell cycle-specific, or
   specific for endothelial cells, smooth muscle cells or macrophages, or
   specific for endothelial cells, smooth muscle cells or macrophages and cell cycle-specific
Structural genes for the inhibition of coagulation or for the promotion of fibrinolysis, for example for
   tissue plasminogen activator (tPA)
   urokinase-type plasminogen activator (uPA)

hybrids of tPA and uPA
protein C
hirudin
serine proteinase inhibitors (serpins), such as
C-1S inhibitor
α1-antitrypsin
antithrombin III
tissue factor pathway inhibitor (TFPI)
Structural genes for promoting coagulation, for example for
F VIII
F IX
von Willebrand factor
F XIII
PAI-1
PAI-2
Structural genes for angiogenesis factors, for example for
VEGF
FGF
Structural genes for lowering blood pressure, for example for
kallikrein
endothelial cell nitric oxide synthase
Structural genes for the inhibition of the proliferation of smooth muscle cells following injury to the endothelial layer, for example for
an antiproliferative, cytostatic or cytotoxic protein or for an enzyme for cleaving precursors of cytostatic agents, thereby forming cytostatic agents, as already cited above (under tumour), and fusion proteins of these active compounds together with antibodies or antibody fragments which are specific for muscle cells.
Structural genes for other blood plasma proteins, for example for
albumin
C1 inactivator
serum cholinesterase
transferrin
α1-antitrypsin
f) Therapy of Metabolic Diseases and Genetic Disease
Target cells:
endothelial cells
muscle cells
liver cells
bronchial epithelial cells
stroma cells, or
macrophages
Promoters:
non target cell-specific, or
target cell-specific
Structural genes, for example for:
the transmembrane conductance regulator (CFTCR) in association with cystic fibrosis
the gene of Fanconi's anaemia
uroporphyrinogen III synthetase
iduronate 2-sulphatase (mucopolysaccharidosis type II)
β-glucuronidase (mucopolysaccharidosis VIII)
glucocerebrosidase (Gaucher's disease)
phenylalanine hydroxylase
dystrophin (Duchenne-type muscular dystrophy)
insulin receptor
human growth hormone
surfactant SP-A and SP-B-associated protein
LDL receptor
apolipoprotein B mRNA-editing protein
adenosine deaminase
g) Inoculations
Target cells:
muscle cells, or
macrophages
Promoters:
non target cell-specific, or
target cell-specific, or
target cell-specific and cell cycle-specific
Structural genes for the prophylaxis of infectious diseases The possibilities of preparing effective vaccines conventionally are limited (Brown, Int. J. Technol. Assessm. Health Care 10, 161 (1994), Ellis, Adv. Exp. Med. Biol. 327, 263 (1992), Arnon et al., FASEB J. 6, 3265 (1992)).

The technology of DNA vaccines was consequently developed. However, these DNA vaccines raise questions with regard to the strength of their efficacy (Fynan et al., Int. J. Immunopharm. 17, 79 (1995); Donnelly et al., Immunol. 2, 20 (1994)).

In accordance with this invention, the self-enhancing expression system increases the efficacy of the DNA vaccines.

The DNA to be selected as the active substance is the DNA for a protein which is formed by the infectious agent and which, by means of eliciting an immune reaction, i.e. by means of antibody binding and/or by means of cytotoxic T lymphocytes, leads to the neutralization and/or destruction of the agent. So-called neutralization antigens of this nature are already employed as vaccination antigens (see review in Ellis, Adv. Exp. Med. Biol. 327, 263 (1992)). The following studies provide examples of DNA sequences which encode neutralization antigens:

influenza A virus antigen
(Ulmer et al., Science 259, 1745 (1993), Robinson et al., Vaccine 11, 957 (1993), Fynan et al., Int. J. Immunopharmac. 17, 79 (1995))
HIV antigens
(Wang et al., PNAS USA 90, 4156 (1993))
rabies virus antigen
(Donnelly et al., Immunol. 2/1, 20 (1994))
HSV (herpes simplex virus) antigen
(Fleckenstein et al., Nature 274, 57 (1978))
RSV (respiratory syncytial virus) antigen
(Du et al., Bio/Tech. 12, 813 (1994), Hall, Science 265, 1393 (1993))
parainfluenza virus antigen
(Du et al., Bio/Techn. 12, 813 (1994))
rotavirus antigen
(Albert et al., J. Clin. Microbiol. 25, 183 (1987), Anderson et al., J. Infect. Dis. 153, 823 (1986), Battaglia et al., J. Infect. Dis. 155, 140 (1987), Chanock et al., J. Infect. Dis. 148, 49 (1983), Dyall-Smith et al., J. Virol. 38, 1099 (1981), Glass et al., Science 265, 1389 (1994))
VZV (varicella zoster virus) antigen
(Straus et al., Ann. Intern. Med. 109, 438 (1988), Gershon, Pediatr. Infect. Dis. 2, 171 (1991), Kinchington et al., J. Virol. 64, 4540 (1990))
CMV (cytomegalovirus) antigen
(Plotkin, Science 265 1383 (1994))

measles virus antigen
(Katz and Kellin, Science 265, 1391 (1994))
HPV (human papillomavirus) antigen
(Tindl and Frazer, Curr. Topics Microbiol. Immunol. 186, 217 (1994))
HBV (hepatitis B virus) antigen
(Valenzuela et al., Nature 280, 815 (1979), Heerman et al., J. Virol. 52, 396 (1984))
HCV (hepatitis C virus) antigen
(Cerny et al., Curr. Topics Microbiol. Immunol. 189, 169 (1994), Esteban et al., Progr. Liver Dis. 10, 253 (1992), Jung et al., Eur. J. Clin. Invest. 24, 641 (1994))
HDV (hepatitis D virus) antigen
(Iwarson, Scand. J. Infect. Dis. 24, 129 (1992), Consolo et al., Nephron. 61, 251 (1992))
HEV (hepatitis E virus) antigen
(Iwarson, Scand. J. Infect. Dis. 24, 129 (1992), Consolo et al., Nephron. 61, 251 (1992))
HAV (hepatitis A virus) antigen
(d'Hondt, Vaccine 10, 48 (1992), Andre, J. Infect. Dis. 171, 33 (1995), Lemon et al., Vaccine 10, 40 (1992), Melnick et al., Vaccine 10, 24 (1992), Flehmig, Baillieres Clin. Gastroenterol. 4, 707 (1990))
Vibrio cholera antigen
(Levine and Kaper, Vaccine 11, 207 (1993))
Borrelia burgdorferi antigen
(Schaible et al., Immunol. Letters 36, 219 (1993), Wallich et al., Lab. Med. 17, 669 (1993))
Helicobacter pylori antigen
(Crabtree et al., Lancet 338, 332 (1991), Blaser, J. Infect. Dis. 161, 626 (1990), Cover and Blaser, J. Biol. Chem. 267, 10570 (1993), Cover et al., Infect. Immunol. 58, 603 (1990), Dunn et al., J. Biol. Chem. 265, 9464 (1990), Dunn et al., Infect. Immunnol. 60, 1946 (1992), Lage et al., Acta Gastroenterol. Belg. 56 (suppl.), 61 (1993), Mobley et al., Scand. J. Gastroint. 26 (suppl. 187), 39 (1991))
malaria antigen
(Nussenzweig and Long, Science 265, 1381 (1994), Maurice, Science 267, 320 (1995), Enders et al., Vaccines 10, 920 (1992), Knapp et al., Infect. Imm. 60, 2397 (1992)).

However, within the meaning of the invention, active substances of this nature also include the DNA for an antiidiotype antibody, or its antigen- binding fragments, whose antigen-binding structures (the complementarity-determining regions) constitute copies of the protein structure or carbohydrate structure of the neutralization antigen of the infectious agent.

Antiidiotpe antibodies of this nature can, in particular, replace carbohydrate antigens in the case of bacterial infectious agents.

Antiidiotypic antibodies of this nature, and their cleavage products, have been reviewed by Hawkins et al. (J. Immunother. 14, 273 (1993)) and Westerink and Apicella (Springer Seminars in Immunopathol. 15, 227 (1993)).

Structural genes for "tumour vaccines"
These include antigens on tumour cells. Antigens of this nature have been reviewed, for example, by Sedlacek et al., Contrib. to Oncol. 32, Karger Verlag, Munich (1988) and Contrib. to Oncol 43, Karger Verlag, Munich (1992).

Other examples are constituted by the genes for the following antigens or for anti-idiotypic antibodies corresponding to the following antigens:
sialyl Lewis
peptides on tumours which are recognized by T cells
proteins expressed by oncogenes
blood group antigens and their precursors
antigens on polymorphic epithelial mucin and other tumour-associated mucins
antigens on heat shock proteins
gangliosides h) The Therapy of Chronic Infectious Diseases
Target cell:
liver cell
lymphocyte and/or macrophage
epithelial cell
endothelial cell
Promoters:
virus-specific
cell-specific
virus-specific or cell-specific and cell cycle-specific
Structural genes, for example for
a protein which exhibits cytostatic or cytotoxic effects. (Examples of cytotoxic or cytostatic proteins have already been cited in the section entitled Tumour therapy.)
an enzyme (in this regard, see the section entitled Tumour therapy) which cleaves a precursor of an antiviral or cytotoxic substance, thereby forning the active substance.
Structural genes for antiviral proteins
cytokines and growth factors possessing antiviral activity. Examples of these are
IFN-α
IFN-β
IFN-γ
TNFβ
TNFα
IL-1
TGFβ
antibody having a specificity which inactivates the relevant virus, or its $V_H$- and $V_L$-containing fragments, or its $V_H$ and $V_L$ fragments which are connected by way of a linker, which fragments can be prepared as already described in Section 2).
Examples of antibodies against viral antigens are:
anti-HBV
anti-HCV
anti-HSV
anti-HPV
anti-HIV
anti-EBV
anti-HTLV
anti-Coxsackie virus
anti-Hantaan virus
a rev-binding protein. These proteins bind to the rev RNA and inhibit rev-dependent posttranscriptional steps in retroviral gene expression. Examples of rev-binding proteins are:
RBP9-27
RBP1-8U
RBP1-8D
pseudogenes of RBP1-8
for ribozymes which digest the mRNA of genes for cell cycle control proteins or the MRNA of viruses.

Ribozymes which are catalytic for HIV have been reviewed, for example, by Christoffersen et al., J. Med. Chem. 38, 2033 (1995).

Structural genes for antibacterial proteins Examples of the antibacterial proteins are antibodies which neutralize bacterial toxins or which opsonize bacteria. Examples of these antibodies are antibodies against C or B meningococci

*E. coli*

Borrelia

Pseudomonas

*Helicobacter pylori*

*Staphylococcus aureus*

7) Combination of Identical or Different Structural Genes

The invention furthermore relates to a self-enhancing, where appropriate pharmacologically controllable, expression system in which the DNA sequences of two identical or two different structural genes [components c) and c')] are combined. For the purpose of expressing the two DNA sequences, the cDNA of an internal ribosome entry site (IRES) is preferably intercalated, as a regulatory element, between the two structural genes.

Examples of IRES sequences of this nature have already been described in Section C5).

Within the meaning of the invention, the following are examples of preferred combinations of structural genes for the therapy of tumours different antiproliferative, cytostatic, cytotoxic, inflammation-inducing proteins, or identical enzymes for cleaving the precursor of a cytostatic agent the therapy of autoimmune diseases different cytokines or receptors having a synergistic effect for inhibiting the cellular and/or humoral immune reaction, or different or identical TIMPs the therapy of deficient haematopoiesis different, hierarchically consecutive cytokines, such as IL-1, IL-3, IL-6 or GM-CSF and erythropoietin, G-CSF or thrombopoietin the therapy of nerve cell damage a neuronal growth factor and a cytokine or the inhibitor of a cytokine the therapy of disturbances of the blood coagulation system and the blood circulation system an antithrombotic agent and a fibrinolytic agent (tPA or uPA), or an antiproliferative, cytostatic or cytotoxic protein (or enzyme) and an antithrombotic agent or a fibrinolytic agent vaccinations an antigen and an immunity-stimulating cytokine, such as

IL-1α

IL-1β

IL-2

GM-CSF

IL-3, or

IL-4 receptor different antigens of one infectious agent or of different infectious agents, or of one tumour type or of different tumour types therapy of viral infectious diseases an antiviral protein and a cytostatic or cytotoxic protein antibodies against different surface antigens of one virus or several viruses therapy of bacterial infectious diseases antibodies against different surface antigens and/or toxins of an organism 8) Insertion of Signal Sequences and Transmembrane Domains In order to facilitate secretion of the expression product of the structural gene, the homologous signal sequence which may be present in the DNA sequence of the structural gene can be replaced with a heterologous signal sequence which improves extracellular secretion.

Thus, for example, the signal sequence for immunoglobulin (DNA position ≦63 to ≧107; Riechmann et al., Nature 332, 323 (1988)) or the signal sequence for CEA (DNA position ≦33 to ≧134; Schrewe et al., Mol. Cell Biol. 10, 2738 (1990); Berling et al., Cancer Res. 50, 6534 (1990)) or the signal sequence of the human respiratory syncytial virus glycoprotein (cDNA for amino acids ≦38 to ≧50 or 48 to 65; Lichtenstein et al., J. Gen. Virol. 77, 109 (1996)) can be inserted.

Alternatively, or in addition, to the signal sequence, a sequence for a transmembrane domain can be inserted in order to anchor the active compound in the cell membrane of the transduced cell which is forming the active compound.

Thus, for example, the transmembrane sequence of the human macrophage colony-stimulating factor (DNA position ≦1485 to ≧1554; Cosman et al., Behring Inst. Mitt. 83, 15 (1988)) or the DNA sequence for the signal and transmembrane regions of human respiratory syncytial virus (RSV) glycoprotein G (amino acids 1 to 63 or their part sequences, amino acids 38 to 63; Vijaya et al., Mol. Cell Biol. 8, 1709 (1988); Lichtenstein et al., J. Gen. Virol. 77, 109 (1996)), or the DNA sequence for the signal and transmembrane regions of influenza virus neuraminidase (amino acids 7 to 35 or the part sequence amino acids 7 to 27; Brown et al., J. Virol. 62, 3824 (1988)) can be inserted between the promoter sequence and the sequence of the structural gene.

In order to enhance translation, the nucleotide sequence GCCACC or GCCGCC can, for example, be inserted at the 3' end of the promoter sequence and directly at the 5' end of the start signal (ATG) of the signal sequence or transmembrane sequence (Kozak, J. Cell Biol. 108, 209 (1989)).

However, the nucleotide sequence for a glycophospholipid anchor can also be inserted for the purpose of anchoring the active compound in the cell membrane of the transduced cells which are forming the active compound.

A glycophospholipid anchor is inserted at the 3' end of the nucleotide sequence for the structural gene, with it being possible for this insertion to be effected in addition to the insertion of a signal sequence.

Glycophospholipid anchors have been described, for example, for CEA (DNA position ≦893 to ≧1079; Berling et al., Cancer Res. 50, 6534 (1990)), for N-CAM (Cunningham et al., Science 236, 799 (1987)) and for other membrane proteins such as Thy-1 (Clissold, Biochem. J. 281, 129 (1992)) or CD16 (Selvaray et al., Nature 333, 565 (1988)).

Ferguson et al. (Ann. Rev. Biochem. 57, 285 (1988)) have published a review of glycophospholipid-anchored membrane proteins.

Another option for anchoring active compounds on the cell membrane, in accordance with the present invention, is that of using a DNA sequence for a ligand/active compound fusion protein. The specificity of the ligand of this fusion protein is directed against a membrane structure on the cell membrane of the selected target cell.

Examples of ligands which bind to the surface of cells are antibodies or antibody fragments which are directed against structures on the surface of, for example:

endothelial cells, including, in particular, antibodies against VEGF receptors, or of muscle cells, such as antibodies against actin, or antibodies against angiotensin II receptors, or antibodies against receptors for growth factors, such as against EGF receptors or against PDGF receptors or against FGF receptors or antibodies against endothelin A receptors The murine monoclonal antibodies are preferably to be employed in humanized form. Fab fragments and recombinant Fv fragments, and their fusion products, are prepared as has already been described above.

The ligands furthermore include all active compounds, such as cytokines or adhesion molecules, growth factors, or their fragments or part sequences thereof, or mediators, which bind to membrane structures or membrane receptors on the particular cell selected. Examples of these ligands are ligands for endothelial cells, such as IL-1, PDGF, bFGF, VEGF, TGGβ (Pusztain et al., J. Pathol. 169, 191 (1993)) or kinin, and derivatives or analogues of kinin. The ligands furthermore include adhesion molecules. Adhesion molecules of this nature, such as Slex, LFA-1, MAC-1, LeCAM-1, VLA-4 or vitronectin, and derivatives or analogues of vitronectin, have already been described for endothelial cells (reviews in Augustin-Voss et al., J. Cell Biol. 119, 483 (1992); Pauli et al., Cancer Metast. Rev. 9, 175 (1990); Honn et al., Cancer Metast. Rev. 11, 353 (1992); Varner et al., Cell Adh. Commun. 3, 367 (1995)).

The ligands also include antibodies, or their fragments, which are directed against tumour-specific or tumour-associated antigens on the tumour cell membrane. Antibodies of this nature have already been described in Section C6a).

The invention also relates to a composition which comprises a novel nucleic acid construct and a coupling substance j) having a binding site for the protein A of component f) and for the protein B of component h). The coupling substance j) is preferably a pharmaceutical composition, in particular a substance which can penetrate through the cell membrane and into the cell, in particular rapamycin, FK506, cyclosporin A, methotrexate, folic acid, retinoic acid, penicillin, 4-hydroxytamoxifen, tamoxifen or tetracycline or a tetracycline/isopropyl-β-D-thiogalactoside conjugate.

The present invention also relates to cells, in particular yeast cells or mammalian cells, which harbour a novel nucleic acid construct and to a process for preparing a novel nucleic acid construct in which the individual components are linked to each other.

The present invention also relates to the use of a novel nucleic acid construct for preparing a drug for local, e.g. transdermal, nasal, oral, gastrointestinal, intrabronchial, intravesicular, intravaginal, intrauterine, subcutaneous, intramuscular, intradermal, periarticular or intraarticular administration, for administration into the cerebrospinal fluid, into the brain, into the liver, into the kidney, into the intestine or into the tongue, or for intraperitoneal, intrapleural or systemic, e.g. intravenous, intraarterial, intraportal or intracardial, administration for the prophylaxis and/or therapy of tumours, leukaemias, automimmune diseases, inflammations, damage to the nervous system, disturbances of the blood coagulation system and blood circulatory system, metabolic diseases, genetic damage, viral or bacterial infectious diseases and/or deficient haematopoiesis and/ or for vaccinating against viral, bacterial or parasitic infections and/or against tumours, and to the use of a cell according to the invention for preparing a drug for local or systemic administration for the prophylaxis and/or therapy of diseases.

DESCRIPTION OF THE FIGURES

FIG. 16 shows a diagram of a self-enhancing, pharmacologically controllable expression system for the cell cycle-specific and pharmacologically controllable expression of β-glucuronidase.

The invention is explained in more detail with the aid of the following examples.

EXAMPLES

1. Construction of a Self-enhancing Expression System

Figure 13:
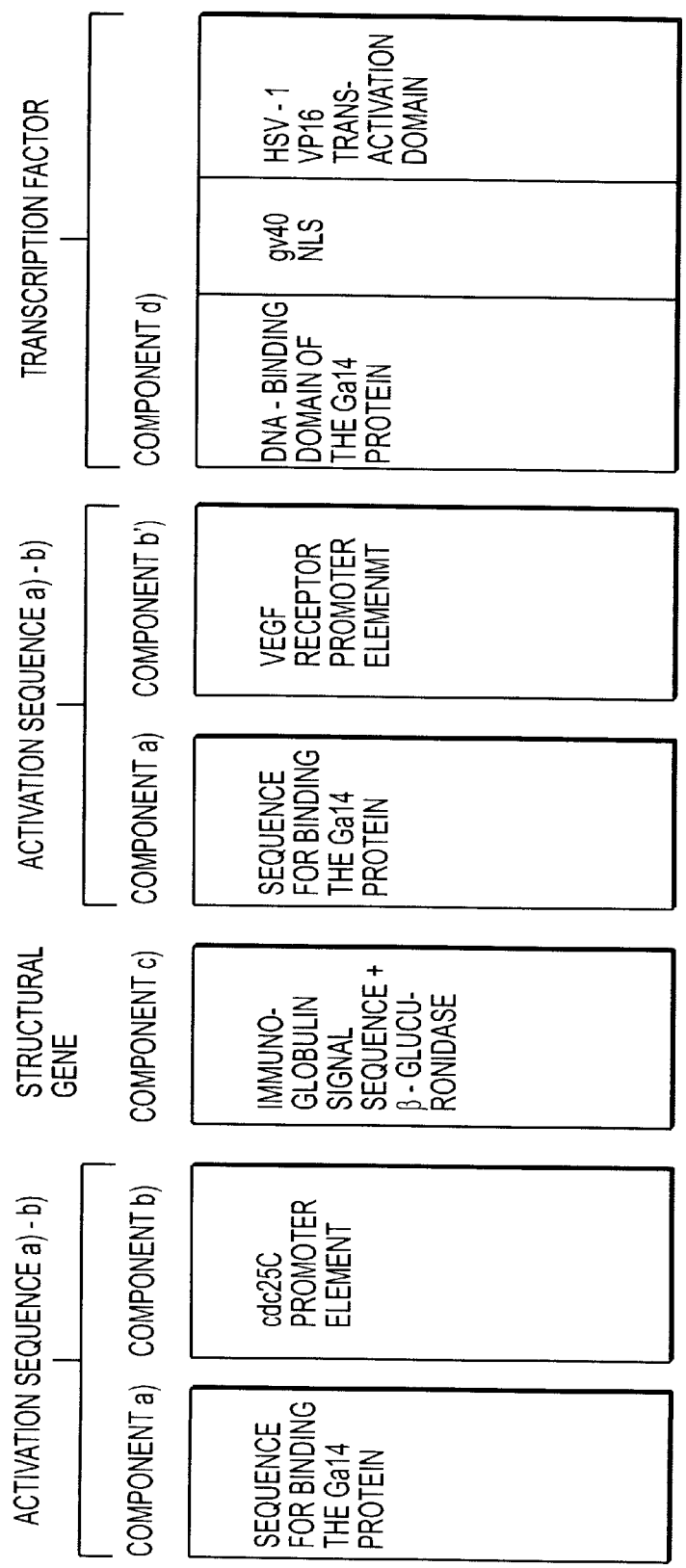
FIG. 13 shows a diagram of a self-enhancing expression system for the cell cycle-specific and cell-specific expression of β-glucuronidase.

A self-enhancing expression system in accordance with the scheme depicted in FIG. 13 is prepared for the purpose of expressing β-glucuronidase in a cell cycle-specific and cell-specific manner.

The DNA sequences of the individual components are joined together, in the 5' to 3' direction, as follows:

component a):
  the sequence (SEQ ID NO:1) [nucleotide sequence: 5'-CGGACAACTGTTGACCG-3'] for binding the Gal4 protein (Chasman and Kornberg, Mol. Cell Biol. 10, 2916 (1990))

component b):
  the promoter sequence of the cdc25C gene [nucleic acids: −290 to +121; Lucibello et al., EMBO J. 14, 132 (1995); Zwicker at al., Nucl. Acids Res. 23, 3822 (1995); EMBO J. 14, 4514 (1995))

component c):
  the sequence GCCACC (Kodak, J. Cell Biol. 108, 229 (1989))
  the cDNA for the immunoglobulin signal peptide [nucleotide sequence $\leq 63$ to $\geq 107$; Riechmann et al., Nature 332, 323 (1988))
  the cDNA for human β-glucuronidase [nucleotide sequence $\leq 93$ to $\geq 1982$; Oshima et al., PNAS USA 84, 685 (1987))

component a'):
  the sequence for binding the Gal4 protein (Chasman and Kornberg, Mol. Cell Biol. 10, 2916 (1990))

component b'):
  the promoter sequence of the VEGF receptor gene [nucleic acids—1195 to +$\geq$100; Morishita et al., J. Biol. Chem. 270, 27948 (1995))

component d):
  the cDNA for the DNA-binding domain of the Gal4 protein [amino acids 1 to 147; Chasman and Kornberg, Mol. Cell Biol. 10, 2916 (1990))
  the cDNA for the SV40 nuclear localization signal (NLS) (SV40 large T; amino acids 126 to 132: (SEQ ID NO:2) PKKKRKV; Dingwall et al., TIBS 16, 478 (1991))
  the cDNA for the HSV-1 VP16 acid transactivation domain (TAD) [amino acids 406 to 488; Triezenberg et al., Genes Developm. 2, 718 (1988); Triezenberg, Curr. Opin. Gen. Developm. 5, 190 (1995))

The individual components of the construct are linked by way of suitable restriction sites which are concomitantly introduced at the termini of the different elements during PCR amplification. The components are linked using enzymes, which are specific for the restriction sites, and DNA ligases which are known to the skilled person. These enzymes can be obtained commercially.

Human umbilical cord endothelial cells and fibroblasts (Wi-38) which are being maintained in culture are transfected with the described plasmid using the method known to the skilled person (Lucibello et al., EMBO J. 14, 132 (1995)), and the quantity of β-glucuronidase which is produced by the endothelial cells is measured using 4-methylumbelliferyl-β-glucuronide as the substrate.

For the purpose of checking the cell-cycle specificity, endothelial cells are synchronized in G0/G1 by removing methionine for 48 hours. The DNA content of the cells is determined in a fluorescence-activated cell sorter following staining with Hoechst 33258 (Hoechst A G, Frankfurt) (Lucibello et al., EMBO J. 14, 132 (1995)).

The following results are obtained:
It is not possible to detect any increase in β-glucuronidase in transfected fibroblasts as compared with untransfected fibroblasts.
Transfected endothelial cells express markedly more β-glucuronidase than do untransfected endothelial cells.
Proliferating endothelial cells (DNA>2S) secrete markedly more β-glucuronidase than do endothelial cells which are synchronized in G0/G1 (DNA=2S).

Consequently, the self-enhancing expression system which has been described leads to a cell-specific, cell cycle-dependent expression of the structural gene β-glucuronidase.

The strength of the expression due to the novel self-enhancing expression system is now compared with that due to two expression systems which are not self-enhancing. These latter systems are prepared in accordance with the schemes depicted in FIGS. 14 and 15.

In this case, the constituents of components b), b') and c) are identical, as already described for the scheme depicted in FIG. 13.

The individual components of the construct are linked by way of suitable restriction sites, which are concomitantly introduced at the termini of the different elements during PCR amplification. The components are linked using enzymes, which are specific for the restriction sites, and DNA ligases which are known to the skilled person. These enzymes can be obtained commercially.

The nucleotide construct which has been prepared in this way is cloned into pUC18/19 or Bluescript-derived plasmid vectors.

Human umbilical cord endothelial cells which are being maintained in culture are transfected with the described plasmids using the method known to the skilled person (Lucibello et al., EMBO J. 14, 132 (1995)), and the quantity of β-glucuronidase which is produced by the endothelial cells is measured using 4-methylumbelliferyl-β-glucuronide as the substrate.

The following results are obtained:
Proliferating endothelial cells which are transfected with the plasmid comprising the nucleic acid construct depicted in FIGS. 14) and 15) express markedly less β-glucuronidase than do proliferating endothelial cells which are transfected with the plasmid comprising the novel nucleic acid construct depicted in FIG. 13).

The self-enhancing expression system which has been described gives rise to markedly enhanced expression of the structural gene β-glucuronidase.

Figure 11:
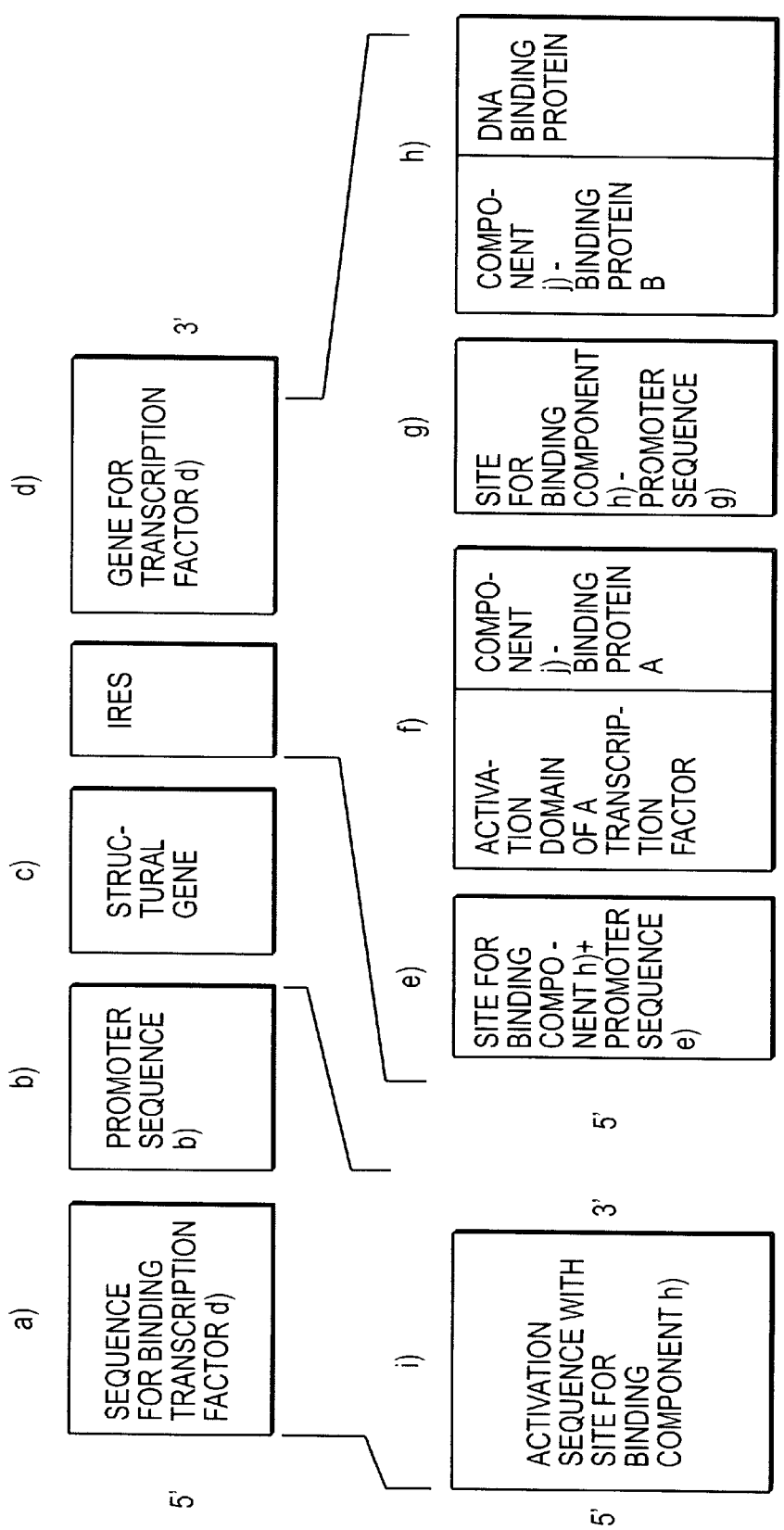
FIG. 11 shows a diagram of the replacement of components a) and b) with component i) and the replacement of component d), together with the IRES region, with the pharmaceutically controllable promoter module containing components e), f), g) and h).
Figure 12:
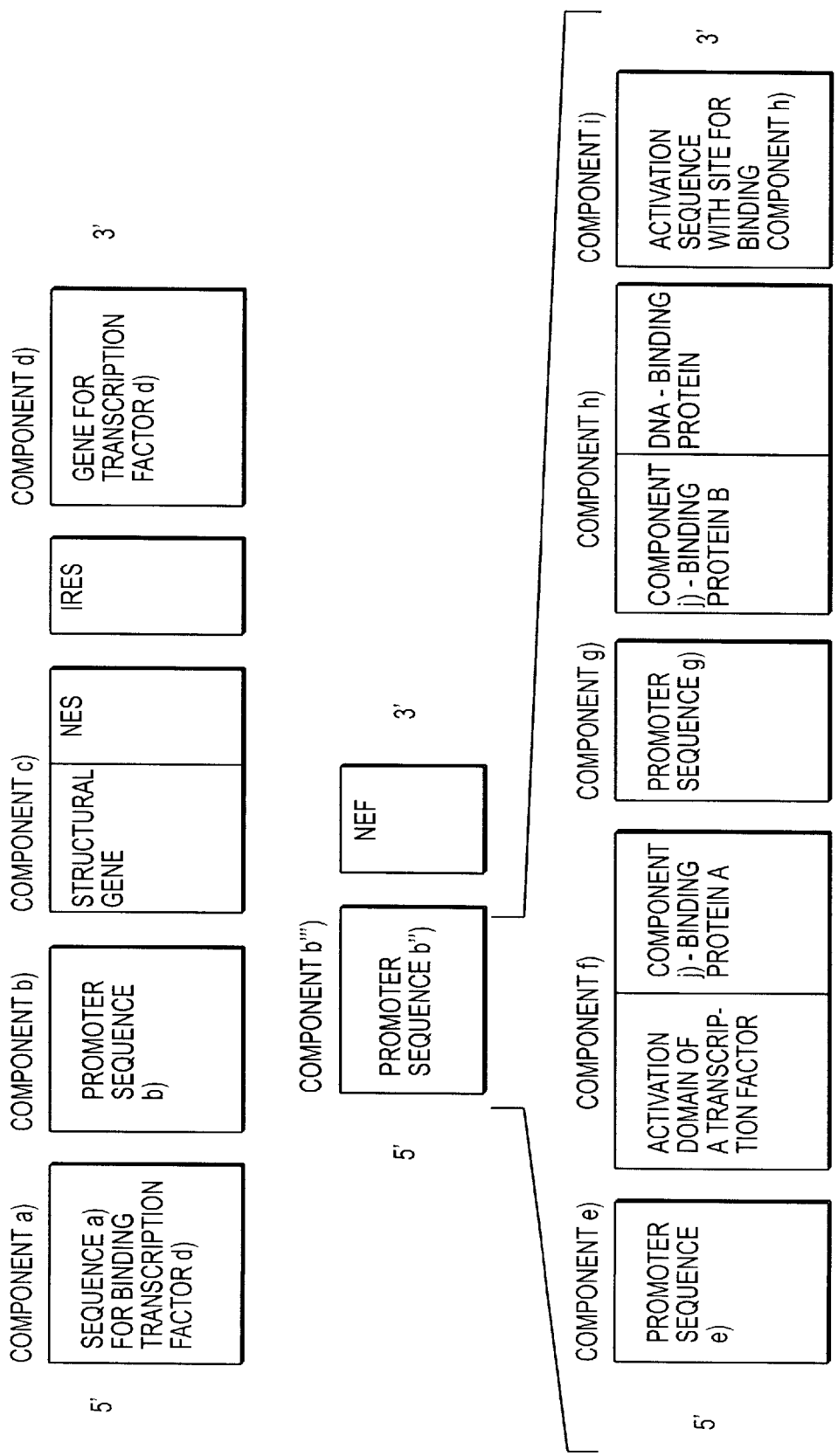
FIG. 12 shows a diagram of the replacement of components b''') with the pharmaceutically controllable promoter module containing components e), f), g), h) and i).

2. Construction of a Self-enhancing, Pharmacologically Controllable Expression System A self-enhancing, pharmacologically controllable expression system, corresponding to the structure shown in the diagram in FIG. 11, is prepared for the cell cycle-specific and pharmacologically controllable expression of β-glucuronidase, as depicted in FIG. 16.

The DNA sequences of the individual components are joined together, in the 5' to 3' direction, as follows:

component i):
  the sequence (SEQ ID NO:1) [nucleotide sequence: 5'-CGGACAACTGTTGACCG-3'] for binding the Gal4 protein (Chasman and Kornberg, Mol. Cell Biol. 10, 2916 (1990))
  the SV40 basal promoter [nucleotides 48 to 5191; Tooze (ed.), DNA Tumor Viruses (Cold Spring Harbor New York, N.Y., Cold Spring Harbor Laboratory)]

component c):
  the sequence GCCACC (Kodak, J. Cell Biol. 108, 229 (1989))
  the cDNA for the immunoglobulin signal peptide [nucleotide sequence $\leq 63$ to $\geq 107$; Riechmann et al., Nature 332, 323 (1988)]
  the cDNA for human β-glucuronidase [nucleotide sequence $\leq 93$ to $\geq 1982$; Oshima et al., PNAS USA 84, 685 (1987)]

component e):
  the sequence for binding the Gal protein (Chasman and Kornberg, Mol. Cell Biol. 10, 2916 (1990))
  the promoter sequence of the cdc25C gene [nucleotides −290 to +121; Lucibello et al., EMBO J. 14, 132 (1995); Zwicker at al., Nucl. Acids Res. 23, 3822 (1995); EMBO J. 14, 4514 (1995)]
component f):
  the cDNA for the herpes virus VP16 activation domain (Greaves et al., J. Virol. 64, 2716 (1990); 65, 6705 (1991))
  the cDNA for recombinant anti-cyclosporin A Fv (A) (protein A)
component g):
  corresponds to component e)
component h):
  the cDNA for recombinant anti-cyclosporin A Fv (B) (protein B)
  the cDNA for the DNA-binding domain of the Gal4 protein [amino acids 1 to 147; Chasman and Komberg, Mol. Cell Biol. 10, 2916 (1990)]
  the cDNA for the SV40 nuclear localization signal (NLS) [SV40 large T; amino acids 126 to 132: (SEQ ID NO:2) PKKKRKV; Dingwall et al., TIBS 16, 478 (1991)]
  the cDNA for the HSV-1 VP16 acid transactivation domain (TAD) [amino acids 406 to 488; Triezenberg et al., Genes Developm. 2, 718 (1998); Triezenberg, Curr. Opin. Gen. Developm. 5, 190 (1995)].

Antibodies against cyclosporin A are prepared as described by Cacalano et al., Mol. Immunol. 29, 107 (1992). For this, cyclosporin A is coupled to bovine serum albumin using 4-benzoylbenzoic acid and UV light. The coupling product is administered several times subcutaneously to Balb/c mice. The spleen cells are isolated 14 days after the last immunization. The mRNA is extracted from these cells using an mRNA extraction kit (from Pharmacia, Freiburg). Reverse transcription is then used to transcribe this mRNA into cDNA with the aid of a cDNA synthesis kit and random hexaoligonucleotides (from Pharmacia, Freiburg). This cDNA serves as the starting material for amplifying the variable heavy chain, or the variable light chain, of the immunoglobulins by means of the polymerase chain reaction (Saiki et al., Science 230, 1350 (1985)) using specific primers (Clackson et al., Nature 352, 624 (1991); Sastry et al., PNAS USA 86, 5728 (1989); Ward et al., Nature 341, 544 (1989); Orlandi et al., PNAS USA 86, 3833 (1989)).

Figure 1:
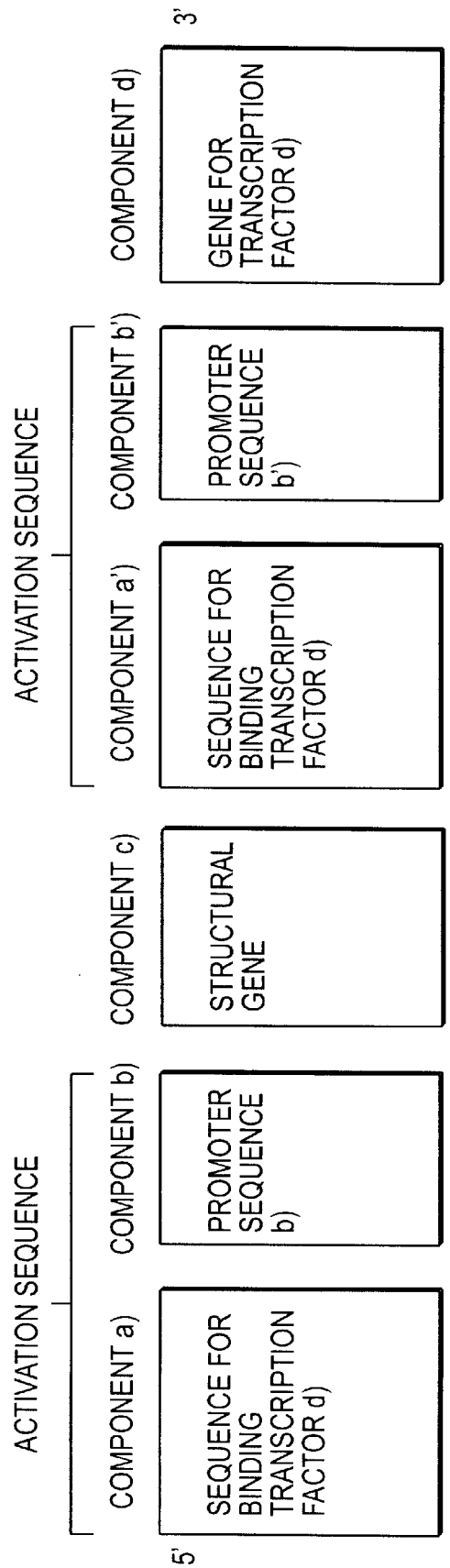
FIG. 1 shows a diagram of the novel nucleic acid construct in its simplest form.
Figure 2:
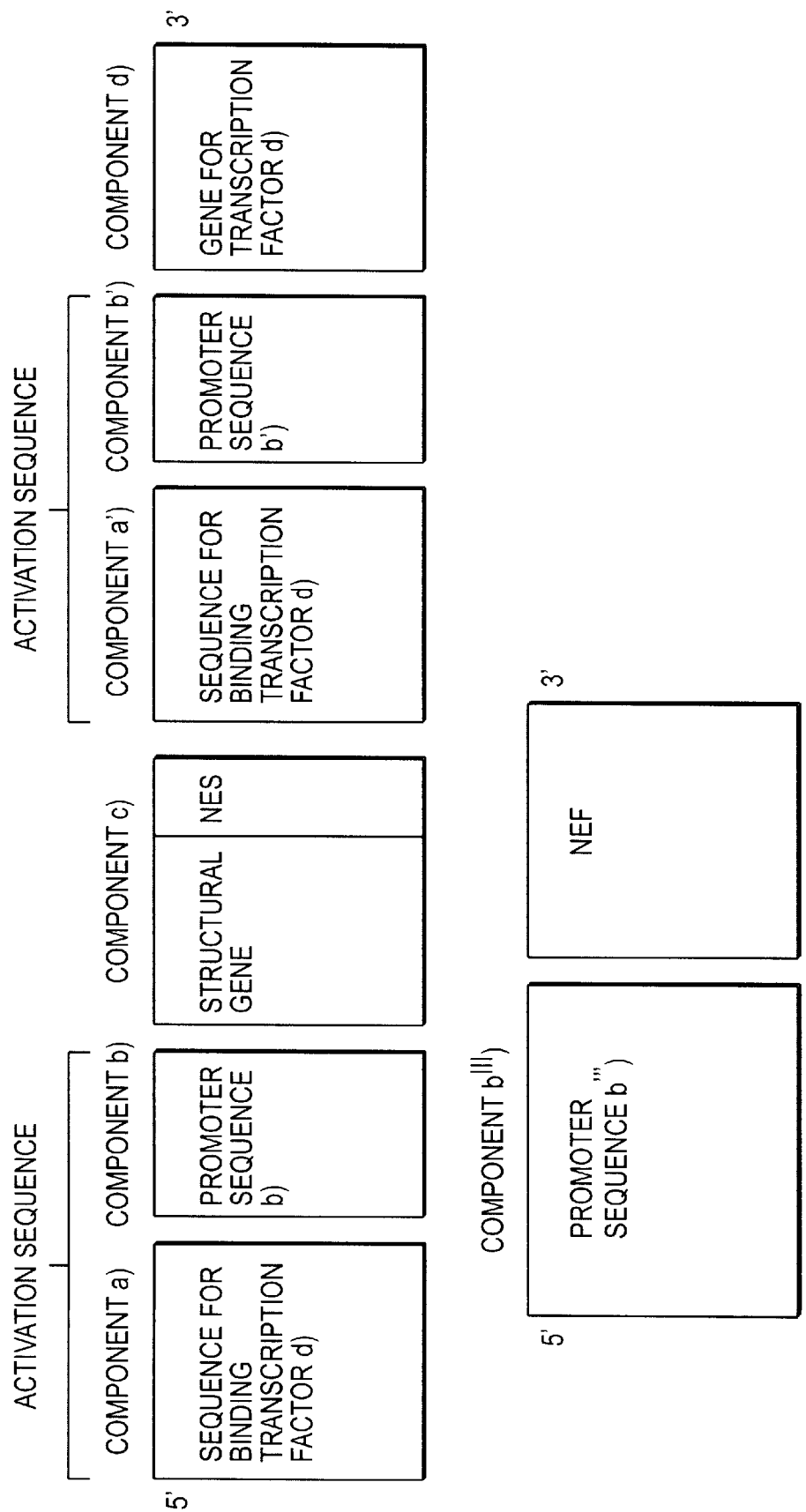
FIG. 2 shows a diagram of the nucleic acid construct depicted in FIG. 1 after having been supplemented with the gene encoding a nuclear export signal (NES) and the gene encoding a nuclear export factor (NEF).
Figure 3:
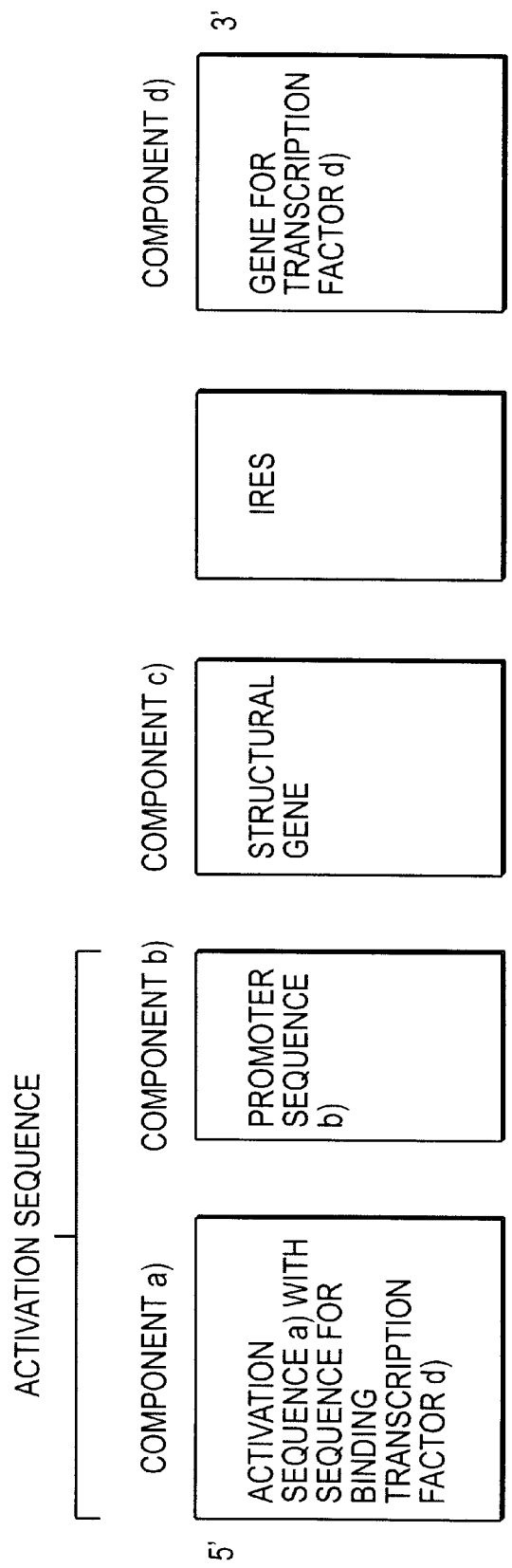
FIG. 3 shows a diagram of the linking of components c) and d) by way of an IRES.
Figure 4:
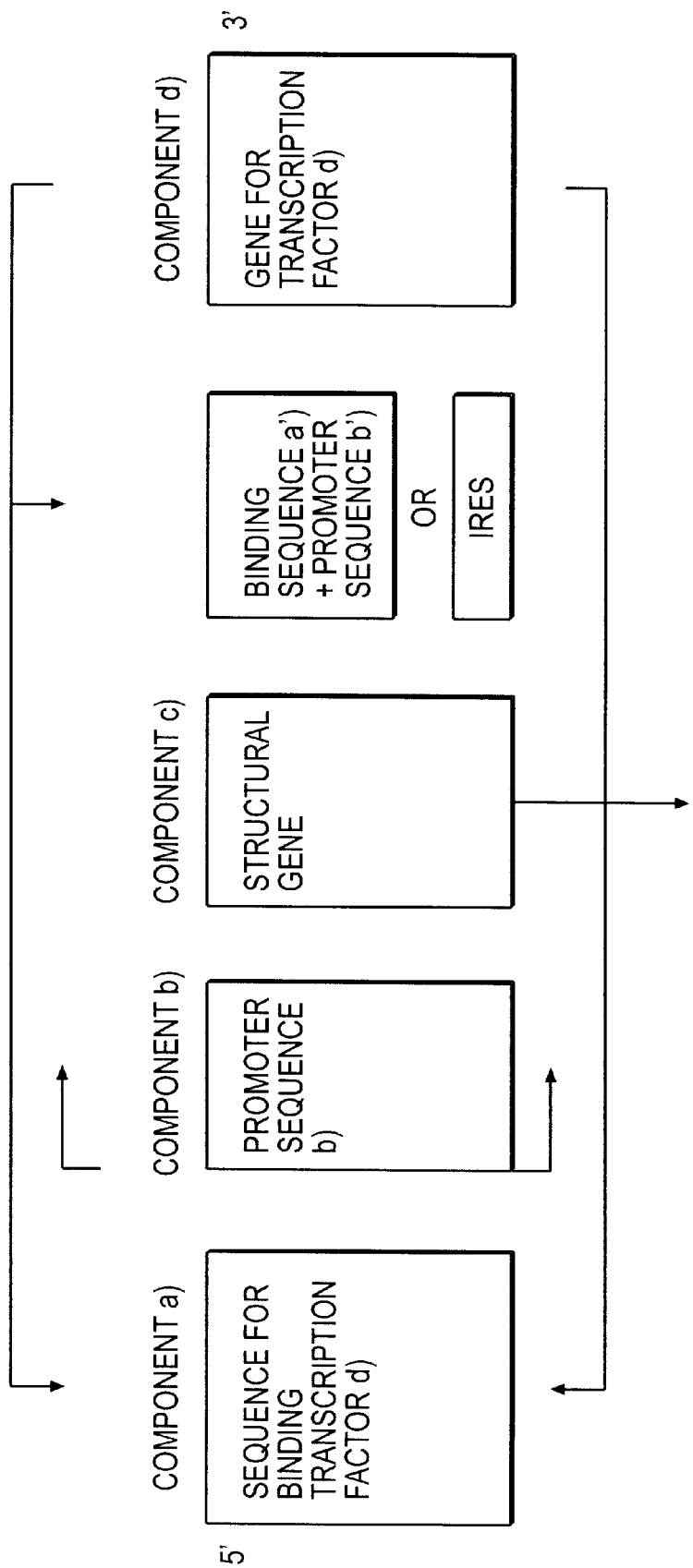
FIG. 4 shows a diagram of the scheme by which the individual components depicted in FIGS. 1–3 react.
Figure 5:
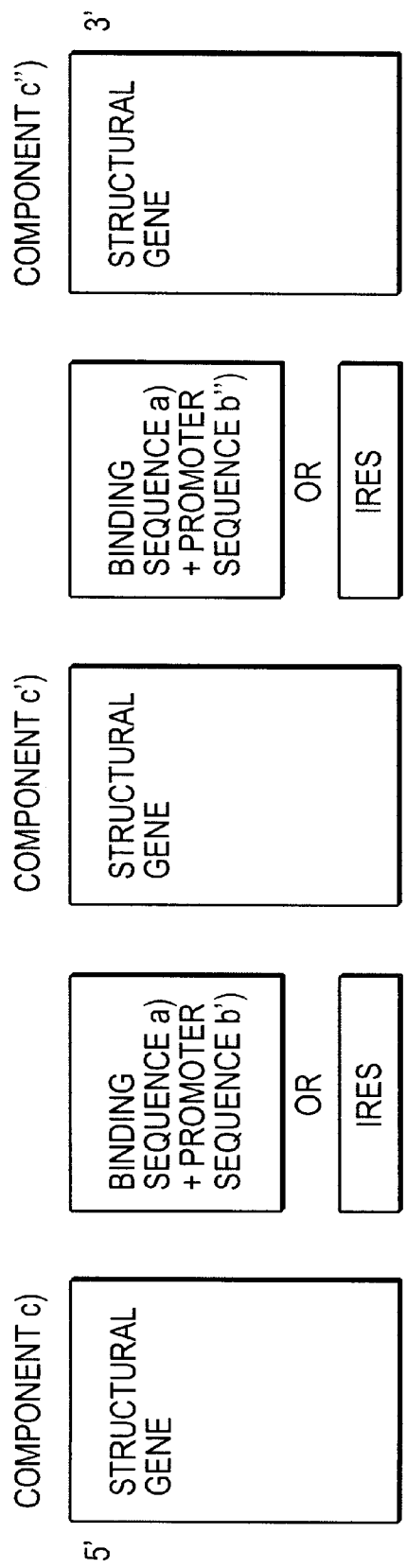
FIG. 5 shows a diagram of the enlargment of the nucleic acid construct with additional structural genes.
Figure 6:
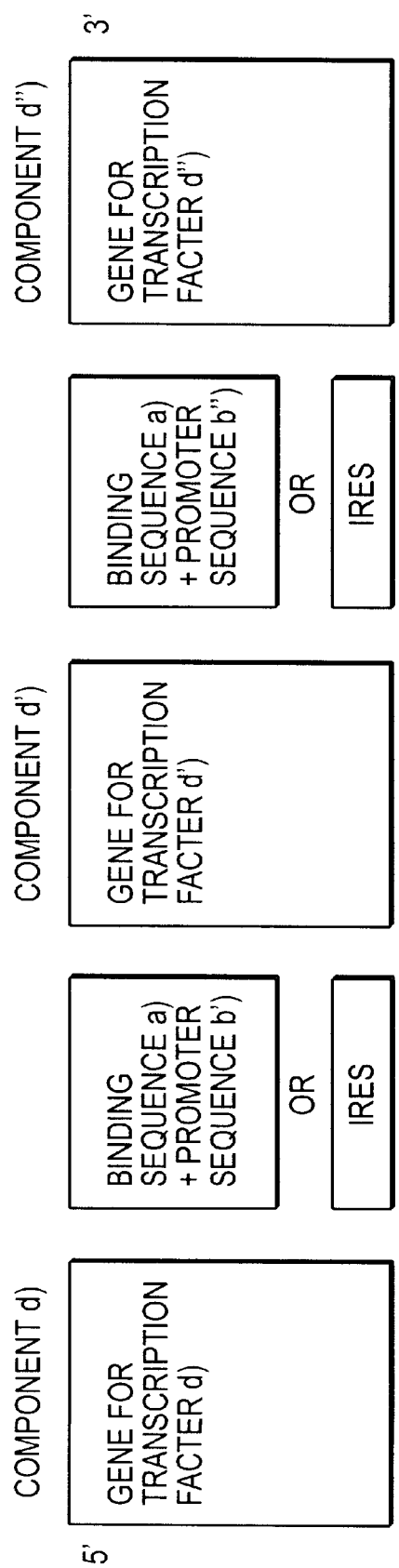
FIG. 6 shows a diagram of the enlargement of the nucleic acid construct with additional genes for the transcription factor protein.
Figure 7:
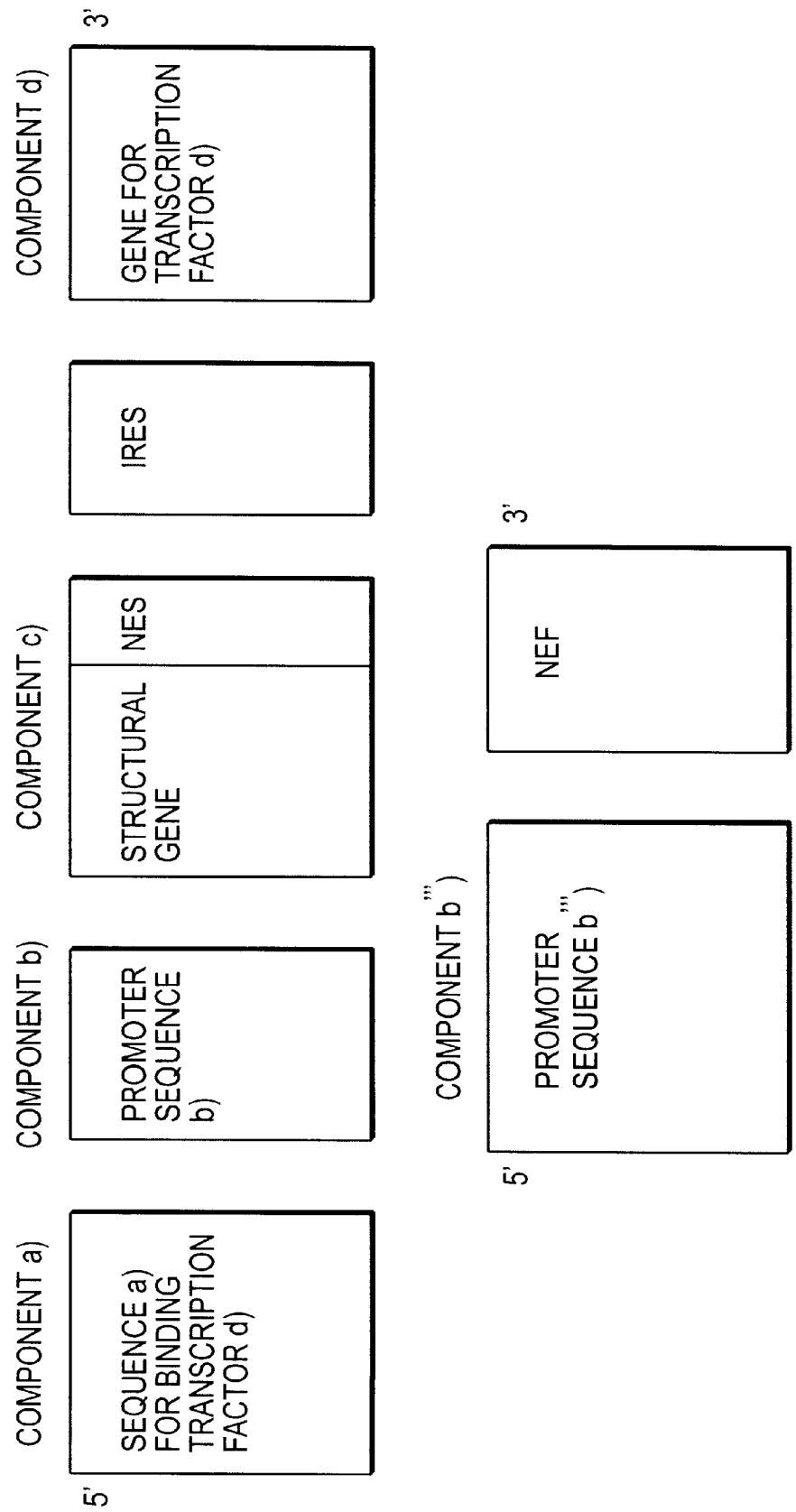
FIG. 7 shows a diagram of the nucleic acid construct depicted in FIG. 3 following supplementation with the genes encoding NES and NEF.
Figure 8:
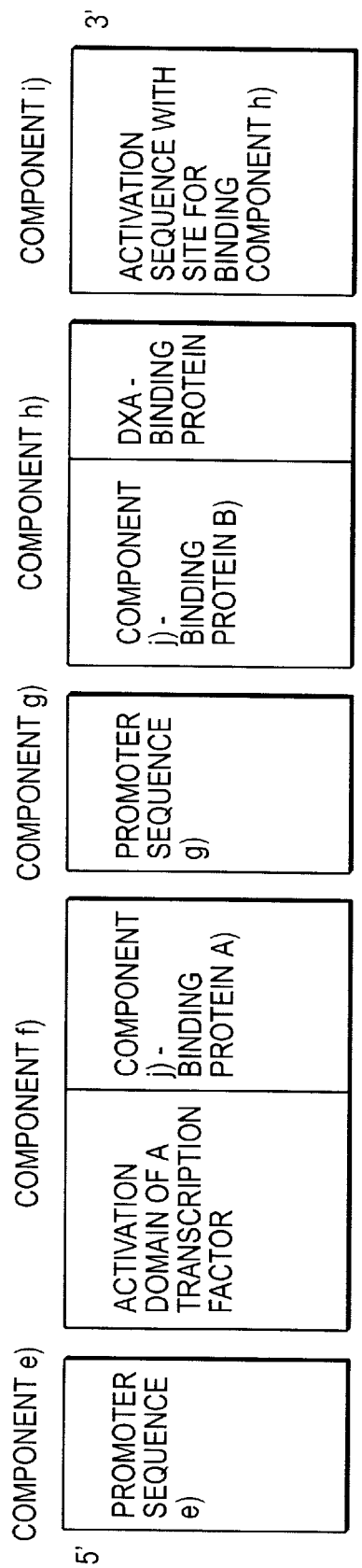
FIG. 8 shows a diagram of a pharmacologically controllable promoter module in its simplest form.
Figure 9:
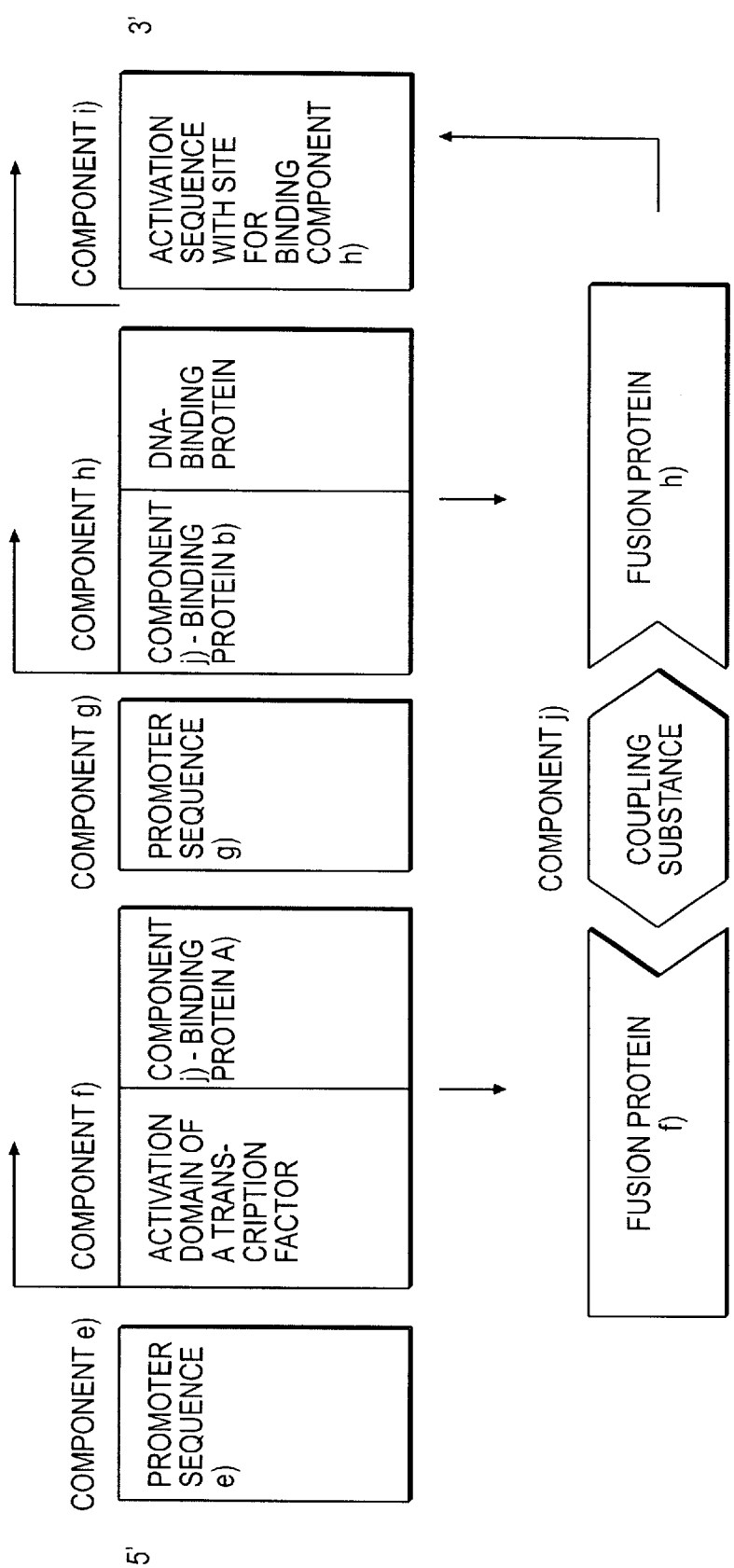
FIG. 9 shows a diagram of the scheme by which the individual components depicted in FIG. 8 react.
Figure 10:
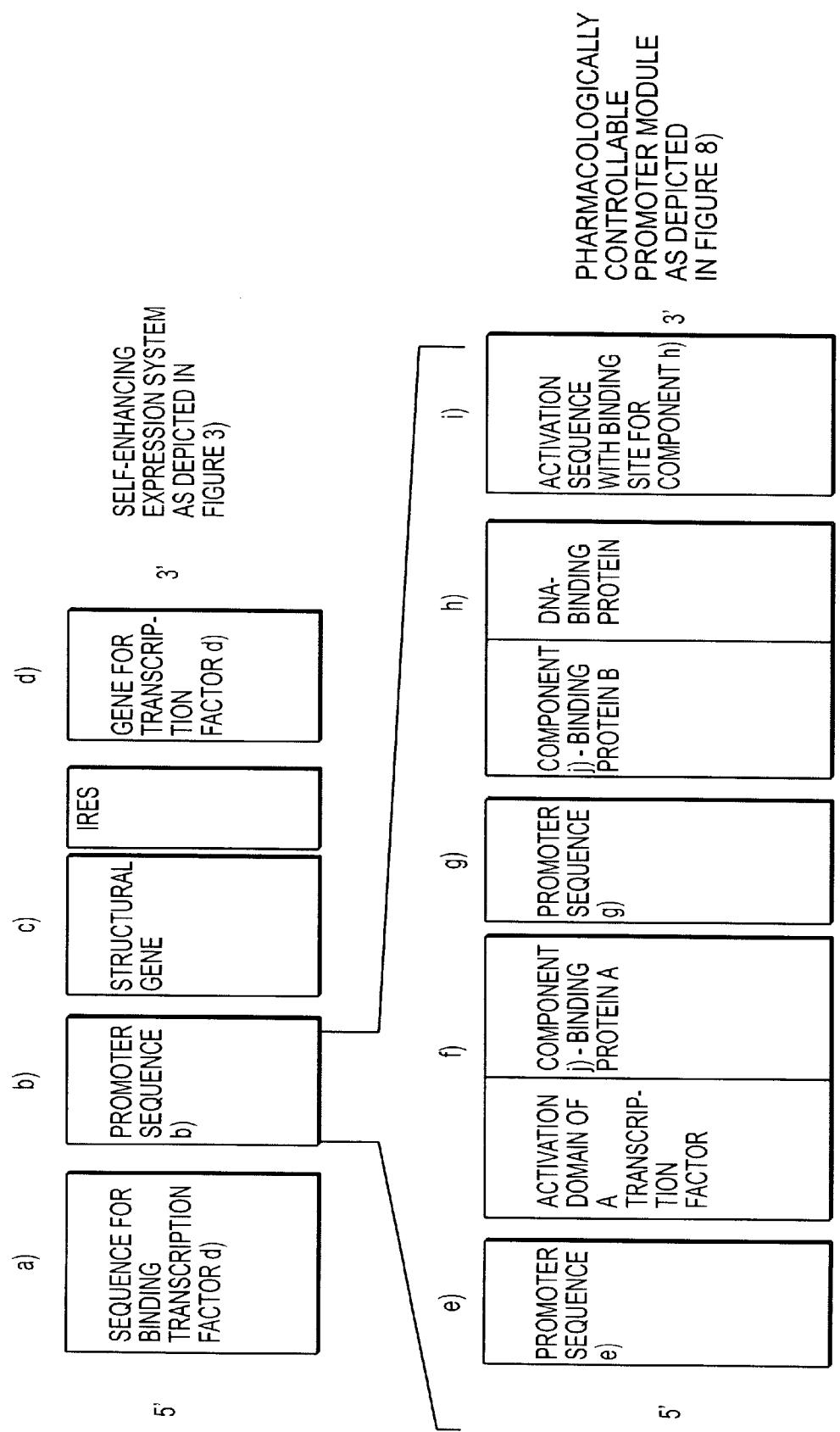
FIG. 10 shows a diagram of a self-enhancing, pharmacologically controllable expression system.

The primers are used to, at the same time, introduce restriction cleavage sites for cloning the fragments into the bacterial expression vector pHENIS (which is derived from pHEN1; Hoogenboom et al., Nucl. Acids Res. 19, 4133 (1991); see FIG. 1)). This vector comprises a pelB signal sequence for periplasmic secretion, a myc tag for detection with the monoclonal antibody 9E10, a histidine tag for purification by means of immobilized metal affinity chromatography (IMAC), as well as a cloning region for the heavy chain and the light chain and a short sequence which encodes a glycine-serine linker of 14 amino acids in length. Fusion with the gene3 protein (g3P) is also effected for the purpose of displaying on the surface of bacteriophages. The heavy and light chains are digested with the appropriate restriction enzymes (VH with SfiI and ShoI; VL with ApaLI and NotI) and cloned consecutively into the vector. This results in a recombinant single-chain Fv fragment comprising the variable heavy chain and variable light chain, which are linked covalently by means of a short peptide sequence.

In conformity with the phage-display of antibody fragments, the antigen-binding domains are cloned in the form of scFv fragments (McCafferty et al., Nature 348, 552 (1990)), as fusion proteins with the filamentous bacteriophage coat protein g3P, into phagemid vectors (Breitling et al., Gene 104, 147 (1994)). Antigen-binding phages are selected on cyclosporin A-loaded plastic receptacles (panning) (Marks et al., J. Mol. Biol. 222, 581 (1991)).

Phages which bind to cyclosporin A are cloned and multiplied and then once again selected on cyclosporin A-loaded plastic receptacles. After selecting four times, two clones (proteins A and B) are chosen which do not inhibit each other's binding to cyclosporin A.

The murine recombinant Fv fragments (proteins A and B) are humanized by specifically replacing the hypervariable regions of human antibodies with the corresponding regions of this murine recombinant Fv fragment (Jones et al., Nature 321, 522 (1987)).

The construct is linked by way of suitable restriction sites, which are introduced at the termini of the different elements during PCR amplification. The linking is effected using enzymes, which are specific for the restriction sites, and DNA ligases which are known to the skilled person. These enzymes can be obtained commercially.

The nucleotide construct which has been prepared in this way is cloned into pUC18/19-derived or Bluescript-derived plasmid vectors.

Human umbilical cord endothelial cells which are being maintained in culture are transfected with the described plasmid using the method known to the skilled person (Lucibello et al., EMBO J. 14, 132 (1995)), and the quantity of β-glucuronidase which is produced by the endothelial cells, with and without the addition of cyclosporin A (0.01 to 1.0 μg/ml of culture medium), is measured using 4-methylumbelliferyl-β-glucuronide as a substrate.

For the purpose of checking the cell-cycle specificity, endothelial cells are synchronized in G0/G1 by removing methionine for 48 hours. The DNA content of the cells is determined in a fluorescence-activated cell sorter following staining with Hoechst 33258 (Hoechst A G, Frankfurt) (Lucibello et al., EMBO J. 14, 132 (1995)).

The following results are obtained:
In the absence of added cyclosporin A, it is not possible to detect any increase in β-glucuronidase in transfected endothelial cells as compared with untransfected endothelial cells.
Following the addition of cyclosporin A, transfected endothelial cells express markedly more β-glucuronidase than do untransfected endothelial cells.
Proliferating endothelial cells (DNA>2S) secrete markedly more β-glucuronidase than do endothelial cells which are synchronized in G0/G1 (DNA=2S).

The self-enhancing expression system which has been described results in an expression of the structural gene β-glucuronidase which is cell cycle-dependent and which can be controlled by adding cyclosporin A.

Figure 14:
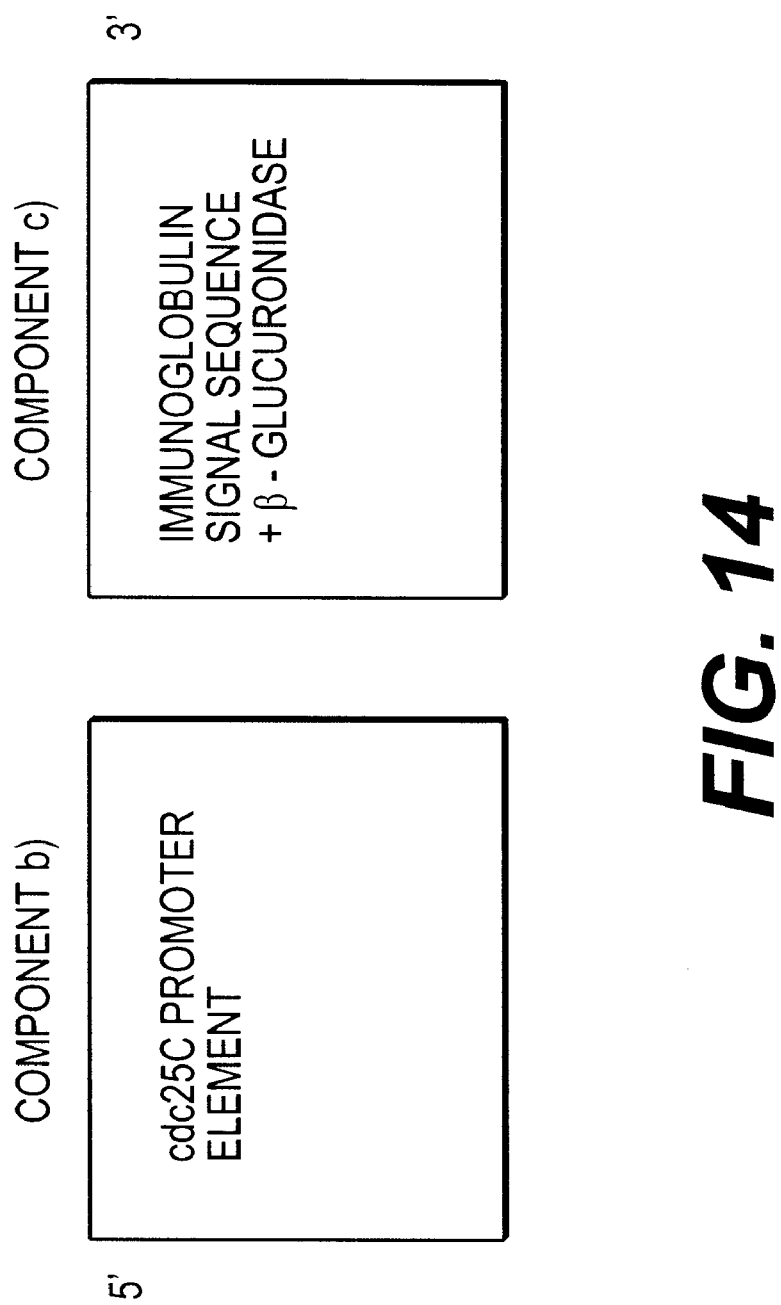
FIGS. 14 and 15 shows diagrams of two expression systems which are not self-enhancing.
Figure 15:
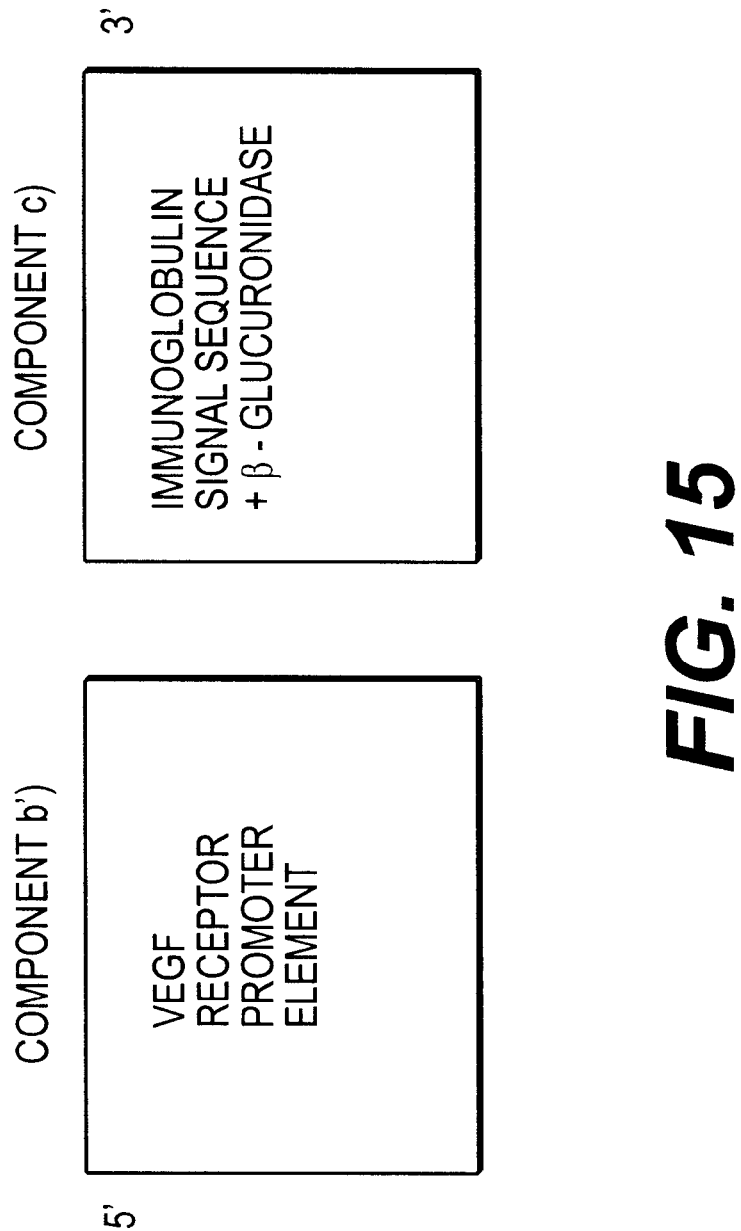

The strength of the expression achieved by the novel, self-enhancing, pharmacologically controllable expression system is greater than that achieved by the non-self-enhancing expression system which was prepared in Example 1) in accordance with the diagram depicted in FIG. 14.

Priority application, 19651443.6 (Federal Republic of Germany), filed Dec. 12, 1996, including the specification, drawing, claims and abstract, is hereby incorporated by reference.

What is claimed is:

1. A nucleic acid construct that comprises:
in a 5' to 3' direction, at least one structural gene; and
at least one gene that encodes a transcription factor protein, wherein said structural gene and said gene that encodes a transcription factor protein are mutually linked by an internal ribosome entry site (IRES) sequence; and
at least one activation sequence comprised of at least one sequence that binds the transcription factor protein and at least one promoter sequence, wherein the binding of said transcription factor protein to said activation sequence activates the expression of said structural gene and the expression of said gene that encodes a transcription factor protein.

2. A nucleic acid construct according to claim 1, further comprising:
   a nuclear export signal sequence appended to the first structural gene;
   a third promoter; and
   a nuclear export factor gene sequence.

3. A nucleic acid construct according to claim 1, comprising two structural genes that encode transcription factors, the two structural genes being mutually linked by an IRES sequence or by an activation sequence.

4. A nucleic acid construct according to claim 3, wherein said transcription factor protein genes are non-identical and transcription factor proteins produced from said genes binds said transcription factor protein binding sequences in the nucleic acid construct.

5. A nucleic acid construct according to claim 1, wherein said activation sequence comprises
   a sequence for binding a transcription factor protein, the sequence selected from the group consisting of the GAL4-protein gene, the LexA-protein gene, the Lac-repressor protein gene, the tetracyclin repressor protein gene, and the ZFHD-1 protein gene;
   a promoter sequence selected from the group consisting of the basal c-fos promoter in combination with the HSV-1 VP16 transactivation domain, the U2 sn RNA promoter in combination with a sequence of the Oct-2 activation domain, and the HSV TK promoter;
and a transcription factor protein gene selected from the group consisting of the DNA-binding domain of the GAL4-protein gene, the DNA-binding domain of LexA-protein gene, the LacI-repressor protein gene, the tetracyclin repressor protein gene, and the ZFHD-1 protein gene.

6. A nucleic acid construct according to claim 5, wherein said transcription factor protein gene comprises a portion that codes for the SV40 nuclear localization signal and the HSV-1 VP 16 acid transactivation domain.

7. A nucleic acid construct according to claim 1, wherein at least one promoter is selected from the group consisting of RNA polymerase III, RNA polymerase II, CMV promoter and enhancer, SV40 promoter, an HBV promoter, an HCV promoter, an HSV promoter, an HPV promoter, an EBV promoter, an HTLV promoter, an HIV promoter, and cdc25C promoter, a cyclin a promoter, a cdc2 promoter, a bmyb promoter, a DHFR promoter and an E2F-1 promoter.

8. A nucleic acid construct according to claim 2, wherein the nuclear export signal and the corresponding nuclear export factor are selected from a rev-responsive element/rev protein of a retrovirus selected from the group consisting of HIV-1, HIV-2, HTLV-1 and HBV.

9. A nucleic acid construct according to claim 1, wherein the structural gene encodes a compound selected from the group consisting of inhibitors of cell proliferation, cytostatic or cytotoxic proteins, enzymes for cleaving prodrugs, antibodies, fusion proteins between antibody fragments and other proteins, cytokines, growth factors, hormones, receptors for cytokines and growth factors, cytokine antagonists, inflammation inducers, coagulation-inducing factors, coagulation inhibitors, fibrinolysis-inducing proteins, angiogenesis inhibitors, angiogenesis factors, hypotensive peptides, blood plasma proteins, insulin receptor, LDL receptor, enzymes whose absence leads to metabolic diseases or immunosuppression, viral antigens, bacterial antigens, parasitic antigens or tumour antigens, an antiidiotype antibody directed against any of the foregoing for these antigens, and a fusion protein derived from any combination of these.

10. A vector comprising the nucleic acid construct of claim 1.

11. A cell which comprises a nucleic acid construct as described in claim 1.

12. A process for preparing a nucleic acid construct as described in claim 1, comprising:
   linking a sequence that binds a transcription factor protein to a promoter sequence to form an activation sequence; and
   linking the activation sequence to at least one structural gene and to at least one gene that encodes a transcription factor protein.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "binding sequence"

(xi) SEQUENCE DESCRIPTION: SEQ ID NO:1:

CGGACAACTG TTGACCG                                           17

(2) INFORMATION FOR SEQ ID NO:2:

(i) SEQUENCE CHARACTERISTICS:
      (A) LENGTH: 7 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:2:

Pro Lys Lys Lys Arg Lys Val
1            5

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "binding sequence"

(xi) SEQUENCE DESCRIPTION: SEQ ID NO:3:

TACTGTATGT ACATACAGTA                                    20

(2) INFORMATION FOR SEQ ID NO:4:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "binding sequence"

(xi) SEQUENCE DESCRIPTION: SEQ ID NO:4:

GAATTGTGAG CGCTCACAAT TC                                22

(2) INFORMATION FOR SEQ ID NO:5:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: other nucleic acid
    (A) DESCRIPTION: /desc = "binding sequence"

(xi) SEQUENCE DESCRIPTION: SEQ ID NO:5:

TCGAGTTTAC CACTCCCTAT CAGTGATAGA GAAAAGTGAA AG                    42

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "binding sequence"

(xi) SEQUENCE DESCRIPTION: SEQ ID NO:6:

TAATGATGGG CG                                                     12

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "binding sequence"

(xi) SEQUENCE DESCRIPTION: SEQ ID NO:7:

GGAAGCAGAC CACGTGGTCT GCTTCC                                      26

(2) INFORMATION FOR SEQ ID NO:8:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AGCAGGTGTT GGGAGGCAGC AGGTGTTGGG AGGCAGCAGG TGTTGGGAGG CAGCAGGTGT    60

TGGGAGGC                                                            68

(2) INFORMATION FOR SEQ ID NO:9:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GGCCGATGGG CAGATAGAGG GGGCCGATGG GCAGATAGAG G                      41